(12) United States Patent
Stern et al.

(10) Patent No.: US 6,994,974 B1
(45) Date of Patent: Feb. 7, 2006

(54) INTRACELLULAR AMYLOID-BETA BINDING (ERAB) POLYPEPTIDE-RELATED ASSAYS

(75) Inventors: David M. Stern, Great Neck, NY (US); Shi Du Yan, New York, NY (US)

(73) Assignee: The trustees of Columbia University in the city of New York, New York, NY (US)

( * ) Notice: Subject to any disclaimer, the term of this patent is extended or adjusted under 35 U.S.C. 154(b) by 0 days.

(21) Appl. No.: 09/394,204

(22) Filed: Sep. 10, 1999

Related U.S. Application Data

(63) Continuation of application No. PCT/US98/04915, filed on Mar. 12, 1998, which is a continuation-in-part of application No. 08/815,225, filed on Mar. 12, 1997, now Pat. No. 6,268,479.

(51) Int. Cl.
G01N 33/53 (2006.01)

(52) U.S. Cl. .......................................... 435/7.1; 435/6

(58) Field of Classification Search ................ 435/7.1, 435/7.2, 6
See application file for complete search history.

(56) References Cited

FOREIGN PATENT DOCUMENTS

WO    WO 9403599    2/1994

OTHER PUBLICATIONS

Rudinger, In "Peptide Hormones" (ed. J.A. Parens) University Park Press Baltimore, pp. 1-7, 1976.*
Borchelt, D. R. et al. (1996) "Familial Alzheimer's Disease-Linked Presenilin 1 Variants Elevate Ab1-42/1-40 Ratio In Vitro and In Vivo." *Neuron*, 17: 1005-1013.
Burke, J. R. et al. (1996) "Huntingtin and DRPLA Proteins Selectively Interact with the Enzyme GAPDH." *Nature Medicine*, 2 (3) : 347-350.
Cai, X-D. et al. (1993) "Release of Excess Amyloid b Protein from a Mutant Amyloid b Protein Precursor." *Science*, 253: 514-516.
Citron, M. et al. (1997) "Mutant Presenilins of Alzheimer's Disease Increase Production of 42-Residue Amyloid b-Protein in both Transfected Cells and Transgenic Mice." *Nature Medicine*, 3 (1) : 67-72.
Huo, Y-M. et al. (1996) "Water-soluble Ab (N-40, N-42) Oligomers in Normal and Alzheimer Disease Brains." *J. Biol. Chem.*, 171 (8) : 4077-4081.
Fuwabara, K. et al. (1996) "Purification and Characterization of a Novel Stress Protein, the 150-kDa Oxygen-regulated Protein (ORP 150), from Cultured Fat Astrocytes and Its Expression in Ischemic Mouse Brain." *J. Biol. Chem.*, 171 (9) : 5025-5032.

Paresce, D. M. et al. (1996) "Microglial Cells Internalize Aggregates of the Alzheimer's Disease Amyloid b-Protein Via a Scavenger Receptor." *Neuron*, 17: 553-565.
Roher, A. E. et al. (1996) "Morphology and Toxicity of Ab-(1-42) Dimer Derived from Neuritic and Vascular Amyloid Deposits of Alzheimer's Disease." *J. Biol. Chem.*, .71 (34) : 20631-20635.
Scheuner, D. et al. (1996) "Secreted Amyloid b-Protein Similar to that in the Senile Plaques of Alzheimer's Disease is Increased in vivo by the Presenilin 1 and 2 and APP Mutations Linked to Familial Alzheimer's Disease." *Nature Medicine*, 2 (8) : 864-870.
Turner, R. S. et al. (1997) "Amyloids b40 and b 42 Are Generated Intracellularly in Cultured Human Neurons and Their Secretion Increases with Maturation." *J. Biol. Chem.*, 271 (15) : 8966-8970.
Wild-Bode, C. et al. (1997) "Intracellular Generation and Accumulation of Amyloid b-Peptide Terminating at Amino Acid 42." *J. Biol. Chem.*, 268 (26) : 16085-16088.
Wolozin, W. et al. (1996) "Participation of Presenilin 2 in Apoptosis: Enhanced Basal Activity Conferred by an Alzheimer Mutation." *Science*, 247: 1710-1713.
Xia, W. et al. (1997) "Enhanced Production and Oligomerization of the 43-Residue Amyloid b-Protein by Chinese Hamster Ovary Cells Stably Expressing Mutant Presenilins." *J. Biol. Chem.*, 172 (12) : 7977-7982.
Yan, S. D. et al. (1994) "Glycated Tau Protein in Alzheimer Disease: A Mechanism for Induction of Oxidant stress." *Proc. Natl. Acad. Sci. USA*, P1 7787-7791.
Yan, S. D. et al. (1995) "Non-enzymatically Glycated Tau in Alzheimer's Disease Induces Neuronal Oxidant Stress Resulting in Cytokine Gene Expression and Release of Amyloid b-Peptide." *Nature Medicine*, . (7) : 693-699.
Yan, S. D. et al. (1996) "RAGE and Amyloid-b Peptide Neurotoxicity in Alzheimer's Disease." *Nature*, 382: 685-691.
Yankner, B. A. et al. (1990) "Neurotrophic and Neurotoxic Effects of Amyloid b-Protein: Reversal by Tachykinin Neuropeptides." *Science*, 250: 279-282.
Adams et al. Initial Assessment of Human Gene Diversity and Expression and Patterns Based Upon 83 Million Nucleotides of cDNA Sequence. Nature. Sep. 23, 1995, vol. 377, No. 6547 supplement, pp. 3-17.

(Continued)

*Primary Examiner*—Robert C. Hayes
(74) *Attorney, Agent, or Firm*—John P. White, Esq.; Cooper & Dunham LLP

(57) ABSTRACT

The present invention provides an isolated nucleic acid encoding an endoplasmic reticulum associated amyloid-beta peptide binding (ERAB) polypeptide. The ERAB polypeptide may comprise human ERAB polypeptide. The present invention provides a purified ERAB polypeptide, as well as a method for treating a neurodegenerative condition in a subject which comprises administering to the subject an agent in amount effective to inhibit ERAB polypeptide binding to amyloid-beta peptide so as to thereby treat the neurodegenerative condition.

5 Claims, 22 Drawing Sheets

OTHER PUBLICATIONS

Furuta et al. Cloning and Expression of cDNA for a Newly Identified Isozyme of Bovine liver 3-Hydroxyacyl-CoA Dehydrognease and its Import into Mitochondria. Biochimica et Biophysica Acta. Feb. 28, 1997, vol. 1350, pp. 317-324.

Yan et al. An Intracellular Protein that Binds Amyloid-β Peptide and Mediates Neurotoxicity in Alzheimer's Disease. Nature. Oct. 16, 1997, vol. 389, pp. 689-695, see entire document.

* cited by examiner pAB002 +pGBT/AB-13
pAB002 +pBA-6
pAB002 +pGBT9
pGAD424 +pGBT/AB-13
pGAD424 +pBA-6
pGAD424 +pGBT9
pTD1 +pVA3

FIGURE 1D

```
                                                  GGAGTGGCCGGCGACAAG  18

ATG GCA GCA GCG TGT CGG AGC GTG AAG GGC CTG GTG GCG GTA ATA ACC  66
 M   A   A   A   C   R   S   V   K   G   L   V   A   V   I   T

GGA GGA GCC TCG GGC CTG GGC CTG GCC ACG GCG GAG CGA CTT GTG GGG  114
 G   G   A   S   G   L   G   L   A   T   A   E   R   L   V   G

CAG GGA GCC TCT GCT GTG CTT CTG GAC CTG CCC AAC TCG GGT GGG GAG  162
 Q   G   A   S   A   V   L   L   D   L   P   N   S   G   G   E

GCC CAA GCC AAG AAG TTA GGA AAC AAC TGC GTT TTC GCC CCA GCC GAC  210
 A   Q   A   K   K   L   G   N   N   C   V   F   A   P   A   D

GTG ACC TCT GAG AAG GAT GTG CAA ACA GCT CTG GCT CTA GCA AAA GGA  258
 V   T   S   E   K   D   V   Q   T   A   L   A   L   A   K   G

AAG TTT GGC CGT GTG GAT GTA GCT GTC AAC TGT GCA GGC ATC GCG GTG  306
 K   F   G   R   V   D   V   A   V   N   C   A   G   I   A   V

GCT AGC AAG ACG TAC AAC TTA AAG AAG GGC CAG ACC CAT ACC TTG GAA  354
 A   S   K   T   Y   N   L   K   K   G   Q   T   H   T   L   E

GAC TTC CAG CGA GTT CTT GAT GTG AAT CTC ATG GGC ACC TTC AAT GTG  402
 D   F   Q   R   V   L   D   V   N   L   M   G   T   F   N   V

ATC CGC CTG GTG GCT GGT GAG ATG GGC CAG AAT GAA CCA GAC CAG GGA  450
 I   R   L   V   A   G   E   M   G   Q   N   E   P   D   Q   G

GGC CAA CGT GGG GTC ATC ATC AAC ACT GCC AGT GTG GCT GCC TTC GAG  498
 G   Q   R   G   V   I   I   N   T   A   S   V   A   A   F   E

GGT CAG GTT GGA CAA GCT GCA TAC TCT GCT TCC AAG GGG GGA ATA GTG  546
 G   Q   V   G   Q   A   A   Y   S   A   S   K   G   G   I   V

GGC ATG ACA CTG CCC ATT GCT CGG GAT CTG GCT CCC ATA GGT ATC CGG  594
 G   M   T   L   P   I   A   R   D   L   A   P   I   G   I   R

GTG ATG ACC ATT GCC CCA GGT CTG TTT GGC ACC CCA CTG CTG ACC AGC  642
 V   M   T   I   A   P   G   L   F   G   T   P   L   L   T   S

CTC CCA GAG AAA GTG TGC AAC TTC TTG GCC AGC CAA GTG CCC TTC CCT  690
 L   P   E   K   V   C   N   F   L   A   S   Q   V   P   F   P

AGC CGA CTG GGT GAC CCT GCT GAG TAT GCT CAC CTC GTA CAG GCC ATC  738
 S   R   L   G   D   P   A   E   Y   A   H   L   V   Q   A   I

ATC GAG AAC CCA TTC CTC AAT GGA GAG GTC ATC CGG CTG GAT GGG GCC  786
 I   E   N   P   F   L   N   G   E   V   I   R   L   D   G   A

ATT CGT ATG CAG CCT TGA AGGGAGAAGGCAGAGAAAACACACGCTCCTCTGCCCTTCCTT  842
 I   R   M   Q   P   *

TCCCTGGGGTACTACTCTCCAGCTTGGGAGGAAGCCCAGTAGCCATTTTGTAACTGCCTACCAGTC  912

GCCCTCTGTGCCTAATAAAGTCTCTTTTTCTCACAAAAAAAAAAAAAAAAAAAAAAAAAAAAAAAA  978

AAA
```

FIGURE 1E-1

```
                 10             20             30              40            50
ERAB  MAAACRSVKGLVAV ITGGAS GLGLATAERLVGQGASAVL LDLPN SGGEAQ
           :::   ::: :::::: :::::::::          :::::
2BHD       MNDLSGKTVI ITGGAR GLGAEAARQAVAAGARVVLADV LADVL DEEGAAT
                 10             20             30              40

60             70             80              90           100
ERAB  AKKLGNNCVFAPADVTSE KDVQTALALAKGKFGRVDVAVNC AGIA VASKT
      :::::::  :::::::: :::::::::::::::::::::   ::::
2BHD  ARELGDAARYQHLDVTIE EDWQRVVAYAREEFGSVDGLVNN AGIS TGMFL
              50             60             70              80            90

110            120            130             140           150
ERAB  YNLKKGQTHTLEDFQRVL D VNLMGTFNVIRLVAGEMGQNEPDQGGQRGVI
             :::::::::: : :::::::::::::            :::
2BHD  ------ETESVERFRKVV D JNLTGVFIGMKTVIPAM------KDAGG--GSI
                 100            110            120             130
```

FIGURE 1E-2

```
              160              180                200
ERAB  INTASVAAFEGGVGQAAYSASKGGIVGMTLPIARDLAPIGIRVMTIAPGL
      : :   :  :  ::  ::::::  : : :  :   ::     :  ::
2BHD  VNISSAAGLMGLALTSSYGASKWGVRGLSKLAAVELGTDRIRVNSVHPGM
            140              160              180

210              230                        
ERAB  FGTPLL--TSLPEKVCNFLASQVPFPSRLGD-PAEYAHLVQAIIEN--PF
      : ::    :         :  ::    :        : :  :
2BHD  TYTPMTAETGIRQEGGNY--PNTPM-GRVGNEPGEIAGAVVKLLSDTSSY
            190              210              230

250
ERAB  LNGEVIRLDGAIRMQP
      : :::    :    :
2BHD  VTGAELAVDGGWTTGPTVKYVMGQ
            240              250
```

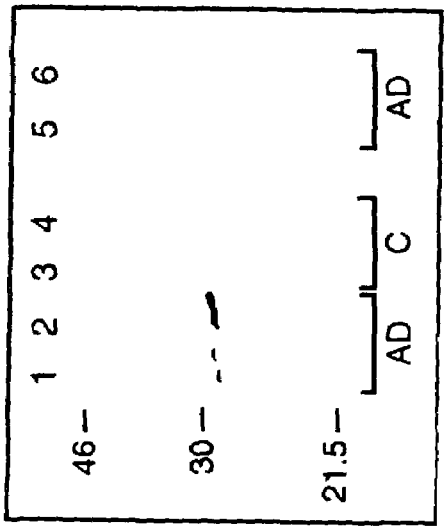
*FIGURE 3D*
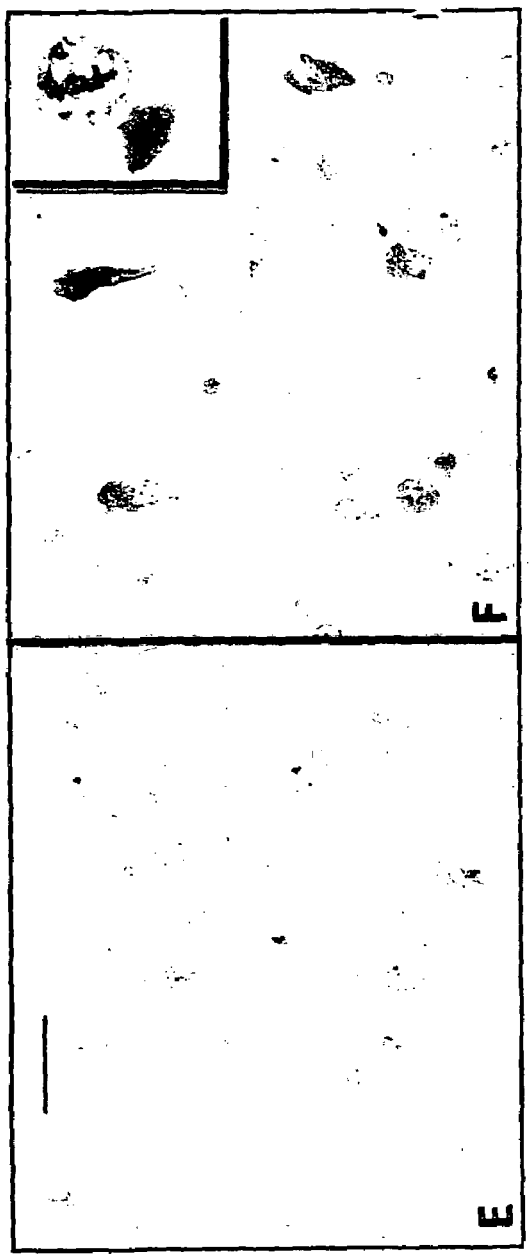
*FIGURE 3E*  *FIGURE 3F-1*  *FIGURE 3F-2*

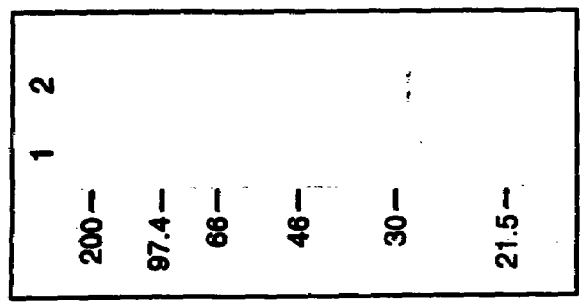
*FIGURE 4A*
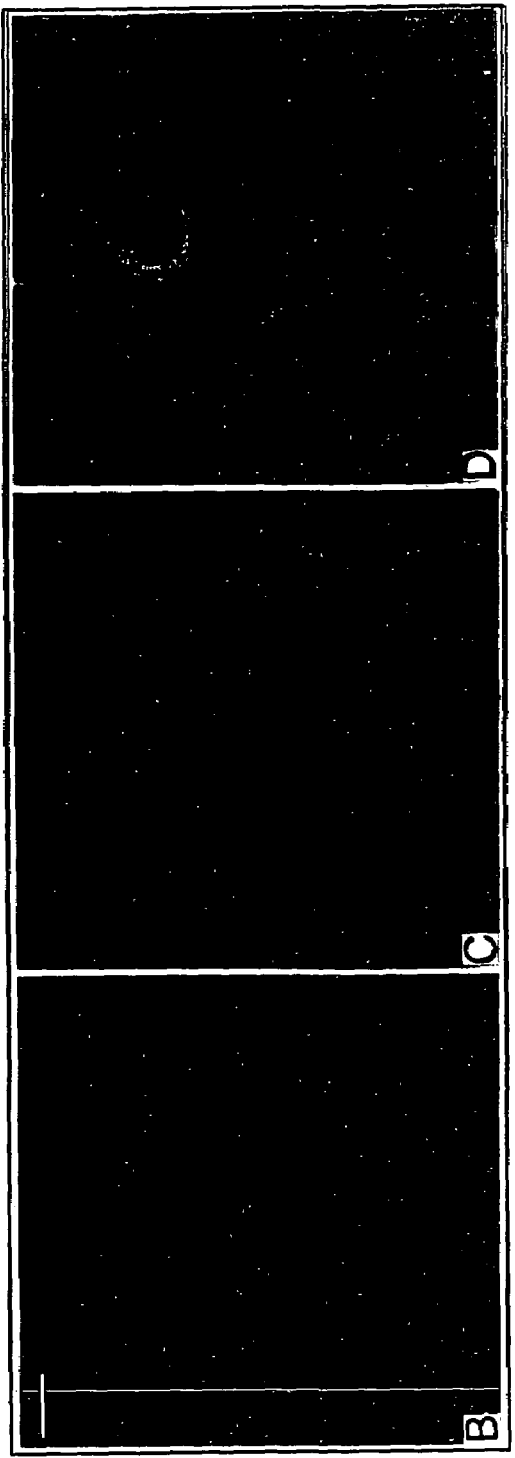
*FIGURE 4B*  *FIGURE 4C*  *FIGURE 4D*

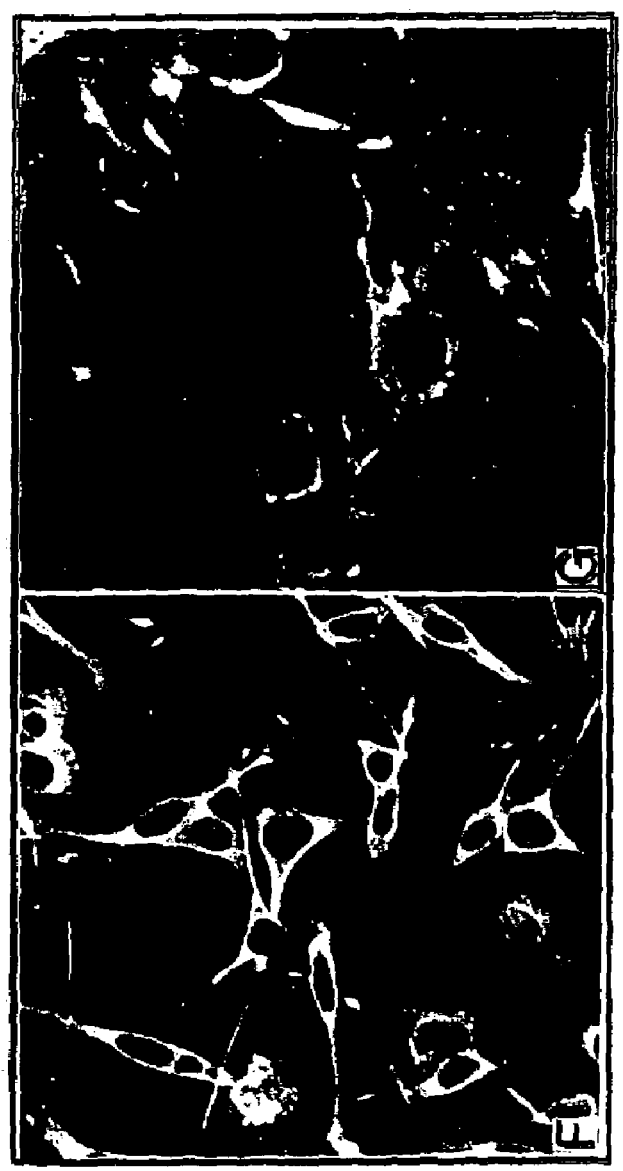
*FIGURE 4G* *FIGURE 4F* *FIGURE 4E*

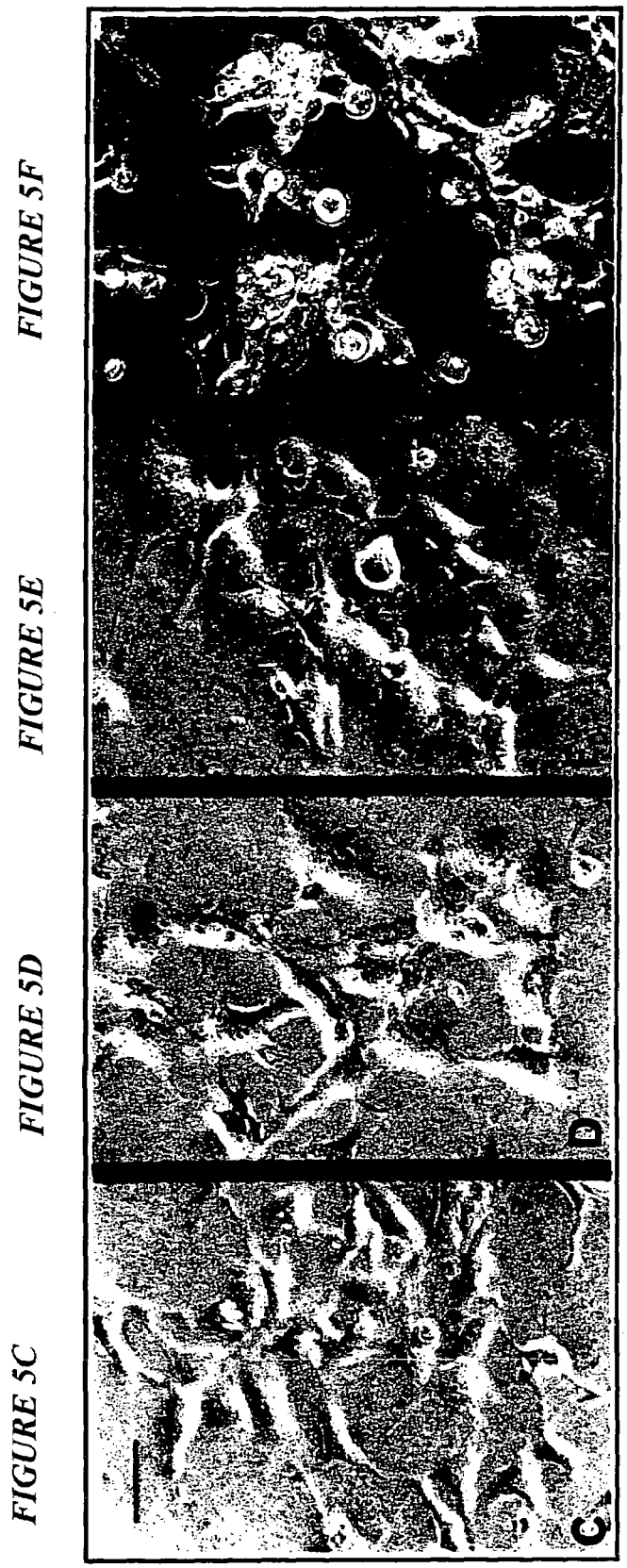

FIGURE 6A FIGURE 6B
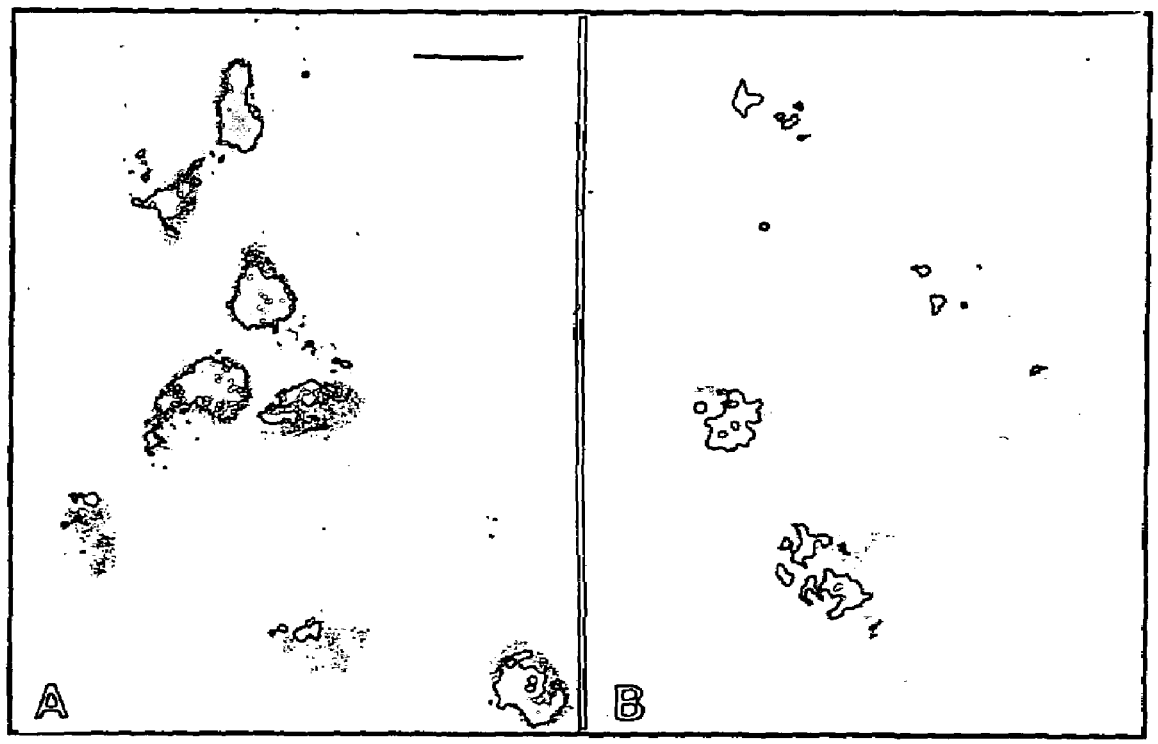

US 6,994,974 B1

INTRACELLULAR AMYLOID-BETA BINDING (ERAB) POLYPEPTIDE-RELATED ASSAYS

This application is a continuation of PCT International Application No. PCT/US98/04915, filed 12 Mar. 1998, designating the United States of America, which is a continuation-in-part of U.S. Ser. No. 08/815,225, filed Mar. 12, 1997, now U.S. Pat. No. 6,268,479, issued Jul. 31, 2001, the contents of which are hereby incorporated by reference into the present application.

The invention disclosed herein was made with Government support under NIH (Aging Institute) Grant No. AG 006902, from the Department of Health and Human Services. Accordingly, the U.S. Government has certain rights in this invention.

Throughout this application, various references are referred to by numbers within parentheses. Disclosures of these publications in their entireties are hereby incorporated by reference into this application to more fully describe the state of the art to which this invention pertains. Full bibliographic citation for these references may be found at the end of this application, preceding the claims, in numerical order corresponding to the numbers within parentheses.

BACKGROUND OF THE INVENTION

Processing of the beta-amyloid precursor protein (APP) leads to a range of proteolyzed forms (1–6), some of which assemble into beta-amyloid fibrils and are cytotoxic. β-amyloid moieties, such as amyloid-beta peptide (Aβ), are closely associated with neuronal dysfunction and death in Alzheimer's disease (AD). Increased expression of amyloid-beta peptide is linked to mutations in APP (6–10) and in presenilins (11–13), both of which occur in familial AD. The mechanisms underlying the cellular stress phenotype brought about in cells by amyloid-beta peptide-derived peptides are likely related to the neurotoxicity leading to dementia. Most attention has been focussed on mechanisms by which extracellular amyloid-beta peptide exerts its effects on cells, since the most visible accumulations of amyloid-beta peptide occur extracellularly in plaques. Amyloid-beta peptide aggregates, especially those that assemble into fibrils, can be cytotoxic by nonspecifically disturbing the integrity of cell membranes, and by elaborating reactive oxygen intermediates (14–15), thereby resulting in elevation of cytosolic calcium eventually followed by cell death (15–16). Cell surface receptors for amyloid-beta peptide (17–19) could also activate signal transduction mechanisms. The receptor RAGE, an immunoglobulin superfamily molecule, is one such neuronal cell surface docking site which binds amyloid-beta peptide and facilitates amyloid-beta peptide-mediated cellular oxidant stress (19).

SUMMARY OF THE INVENTION

The present invention provides an isolated nucleic acid encoding an endoplasmic reticulum associated amyloid-beta peptide binding (ERAB) polypeptide. The ERAB polypeptide may comprise human ERAB polypeptide. The present invention provides a purified ERAB polypeptide, as well as a method for treating a neurodegenerative condition in a subject which comprises administering to the subject an agent in amount effective to inhibit ERAB polypeptide binding to amyloid-beta peptide so as to thereby treat the neurodegenerative condition.

DESCRIPTION OF THE FIGURES

FIGS. 1A, 1B, 1C, 1D, 1E-1 and 1E-2. Identification and cloning of a cell-associated binding protein for amyloid-beta peptide. FIG. 1A. Schematic depiction of fragments of human amyloid precursor protein (APP) cloned into the yeast expression vector pGBT9. The line at the top designates the full-length APP cDNA (numbering is according to the Genbank sequence accession #X06989) and thickened portions indicate the region encoding A4 (APP amino acids 653 to 694). Open boxes show APP fragments encoded by the indicated plasmid fusion proteins. ATG, start codon; TAG, stop codon; E, EcoRI; S, StyI; and B, BamHI. FIG. 1B. Visualization of β-galactosidase reaction product when yeast express the two indicated constructs. The left panel of FIG. 1B demonstrates the presence of yeast on the agar and the right panel of FIG. 1B shows the same area stained for β-galactosidase reaction product. Each experiment is shown in triplicate. pAβ002 is one of three ERAB-containing clones derived from the HeLa cell Matchmaker™ cDNA library. pVA3 indicates murine p53 in pGBT9, pTD1 indicates SV40 large T-antigen in pGAD3F, and the combination of these two plasmids is used as a positive control. FIG. 1C. Quantitative analysis of β-galactosidase gene product from an experiment using the same constructs as in FIG. 1B. FIG. 1D. cDNA sequence and deduced amino acid sequence of the endoplasmic reticulum binding polypeptide (ERAB polypeptide) identified in the yeast two-hybrid system (Seq. Id. Nos. 1 and 2). FIGS. 1E1–1E2. Alignment of ERAB polypeptide deduced amino acid sequence (Sequence Id. No. 3) with that for 20-β-hydroxysteroid dehydrogenase (BHD) (Seq. Id. No. 4). The boxed areas correspond to amino acid domains involved in binding of nicotinamide adenine dinucleotide (NAD). The boxed area with bold letters corresponds to the putative active center of the steroid binding domain. One dot and two dots indicated similar and identical amino acid residues, respectively. Methods: Fragments of human amyloid precursor protein (APP) were cloned into the yeast expression vector pGBT9 (a GAL4 DNA-binding domain hybrid cloning vector; Clontech). The 3'-end of the EcoRI fragment from the APP cDNA was cloned into pGBT9 to generate pGBT/APP-23, which encodes a fusion protein comprising the C-terminus of APP (amino acids 655–751). A stop codon (TGA) was introduced after the sequence of A4 by site-directed mutagenesis and the resulting EcoRI fragment was cloned into pGBT9 to generate pBA-6, which encodes a fusion protein containing A4 peptide sequence (amino acids 3–42). A BamHI site was introduced at the beginning of A4 by PCR amplification and the resulting fragment was subcloned into the unique BamHI site of pGBT9 to generate pGBT/AB-13, the latter encoding a fusion protein with the A4 peptide sequence (amino acids 1–42). The plasmid constructs pBA-6 and pGBT/AB-13 were used as bait to screen human brain and HeLa Matchmaker libraries according to the manufacturer's instructions. Quantitative assay of β-galactosidase activity was performed using o-nitrophenyl β-D-galactopyranoside (ONPG) as substrate.

FIG. 2A. SDS-PAGE (12%; reduced) followed by immunoblotting of TrcHis-ERAB polypeptide (FIG. 2A, lane 1; 2 µg) and TrcHis-chloramphenicol acetyltransferase (CAT; FIG. 2A, lane 2; 2 µg) fusion proteins using anti-ERAB polypeptide IgG (3 µg/ml). FIG. 2A lane 3 has the same sample as in FIG. 2A lane 1, except that free peptide used as immunogen was present at an ≈25-fold molar excess over the antibody. FIGS. 2B and 2C. The indicated concentrations of TrcHis-ERAB polypeptide (FIG. 2B; or in FIG. 2C, 5 µg/well) were incubated in microtiter wells, excess sites on the plastic surface were blocked, and a binding assay was performed by adding $^{125}$I-amyloid-beta peptide (100 nM; 1–40) alone or in the presence of an 100-fold molar excess of unlabelled amyloid-beta peptide (1–40; FIG. 2B). In FIG. 2C, anti-ERAB polypeptide IgG (a-ERAB polypeptide; 10 µg/ml or nonimmune (NI) IgG (10 µg/ml) was added. Specific binding (that observed in wells with $^{125}$I-amyloid-beta peptide alone minus binding observed in wells with $^{125}$I-amyloid-beta peptide+unlabelled amyloid-beta peptide), the mean±SEM of quadruplicate determinations, is shown. FIG. 2D. TrcHis-ERAB polypeptide (5 µg/well) was incubated in microtiter wells, and the binding assay was performed using the indicated concentrations of $^{125}$I-amyloid-beta peptide (1–40) alone or in the presence of excess unlabelled amyloid-beta peptide. Binding was analyzed by nonlinear least squares analysis using the method of Klotz and Hunston (60). FIG. 2E. Competitive binding study: TrcHis-ERAB polypeptide (5 µg/well) was incubated in microtiter wells, and the binding assay employed freshly prepared $^{125}$I-amyloid-beta peptide (100 nM; 1–40). Where indicated one of the following unlabelled competitors was added: freshly prepared synthetic amyloid-beta peptide (1–20), amyloid-beta peptide (1–40), amyloid-beta peptide (25–35), scrambled amyloid-beta peptide (25–35), amyloid-beta peptide purified from AD brain (61), Arg-Gly-Asp-Ser (Seq. ID. No. 5), or amyloid-beta peptide (1–40) incubated for 3 days at 37° C. under conditions to promote aggregation (6) (in each case the competitor was added at 10 µM). FIGS. 2F and 2G. Binding of $^{125}$I-TrcHis-ERAB polypeptide to amyloid-beta peptide (1–42) adsorbed to microtiter wells. In FIG. 2F, the indicated concentration of amyloid-beta peptide (1–42) was incubated in wells, excess sites on the plate were blocked, and the binding assay was performed by adding $^{125}$I-TrcHis-ERAB polypeptide alone or in the presence of an 100-fold molar excess of unlabelled TrcHis-ERAB polypeptide. In FIG. 2G, the binding assay was performed in the presence of the indicated concentration of $^{125}$I-TrcHis-ERAB polypeptide (alone or in the presence of an 100-fold molar excess of unlabelled TrcHis-ERAB polypeptide) in wells with adsorbed amyloid-beta peptide (1–42; 5 µg/well was added). 0 indicates wells coated with albumin alone. The mean±SEM of specific binding of quadruplicates is shown. * indicates p<0.01. Methods: A fusion protein construct was prepared by subcloning an approximately 1116 bp EcoRI fragment (including 318 bp of 3'-untranslated sequence) into the unique EcoRI site of pTrcHis C vector (Invitrogen) to express TrcHis-ERAB polypeptide fusion protein. Following transformation of E. coli with this latter construct, the TrcHis-ERAB polypeptide fusion protein was purified as described by the manufacturer (Invitrogen). Control TrcHis-CAT construct (Invitrogen) was also used to transform E. coli and the fusion protein was purified as above. Antibody to ERAB polypeptide was prepared by immunizing rabbits with ERAB polypeptide-derived peptides, corresponding to residues 100–116 and 133–147, conjugated to keyhole limpet hemocyanin. These antibodies were demonstrated to be specific for ERAB polypeptide (see FIGS. 2A–2G and description), and were used for immunoblotting, immunohistochemistry and functional studies. For immunoblotting shown in FIG. 2A, proteins were subject to reduced SDS-PAGE (12%), electrophoretic transfer to nitrocellulose, and reaction with anti-ERAB polypeptide antibody; sites of anti-ERAB polypeptide IgG binding were detected using the alkaline phosphatase method (Sigma).

$^{125}$I-amyloid-beta peptide (1–40) was radiolabelled as described (19) and $^{125}$I-TrcHis-ERAB polypeptide polypeptide was labeled by the lactoperoxidase method (62). The latter tracer demonstrated a specific radioactivity of 2,000–2,500 cpm/ng, was >95% precipitable in trichloroacetic acid, and migrated as a single band, $M_1 \approx 29$ kDa, on SDS-PAGE. The binding assay to demonstrate direct interaction of ERAB polypeptide and amyloid-beta peptide utilized a modification of a previously described method (19). In brief, the indicated protein, ERAB polypeptide or amyloid-beta peptide, was diluted in carbonate buffer and incubated for 2 hrs at 37° C. (for ERAB polypeptide) or overnight at 4° C. (for amyloid-beta peptide) in Nunc MaxiSorb plates, excess sites in wells were blocked by exposure to albumin-containing solution (1% for 2 hr at 37° C.), and then the radioiodinated tracer alone or in the presence of excess unlabelled material was added in minimal essential medium with bovine serum albumin (1%; Sigma; fraction V, fatty acid-free) at 37° C. Incubation time was 3 hrs, when $^{125}$I-TrcHis-ERAB polypeptide and $^{125}$I-amyloid-beta peptide were the tracers, respectively. Unbound radioactivity was removed by washing wells five times with ice cold phosphate-buffered saline containing Tween 20 (0.05%), and bound radioactivity was eluted by incubation with Nonidet P-40 (1%).

Figure 2A:
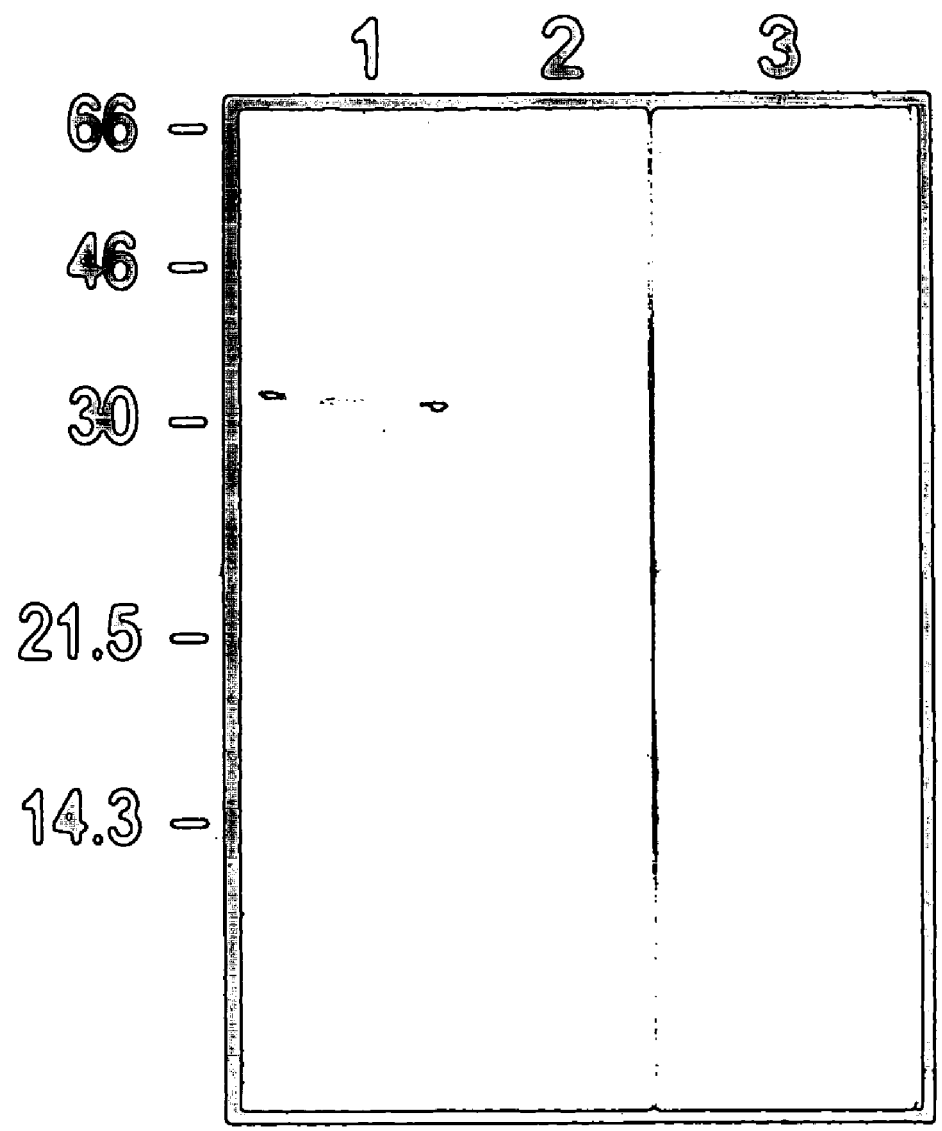
FIGS. 2A, 2B, 2C, 2D, 2E, 2F, and 2G. Expression of ERAB fusion protein: amyloid-beta peptide binding properties.
Figure 2B:
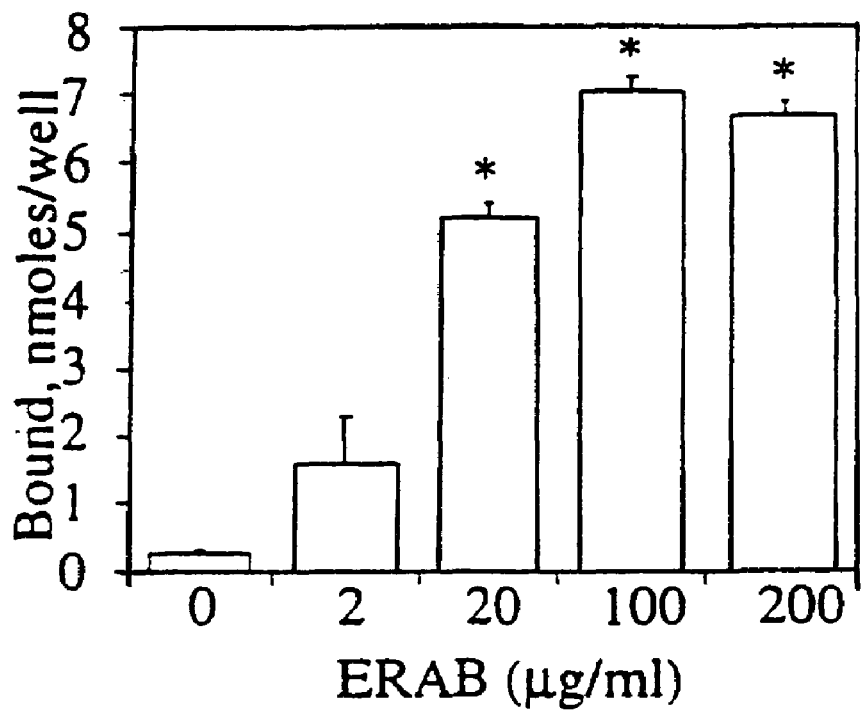
Figure 2C:
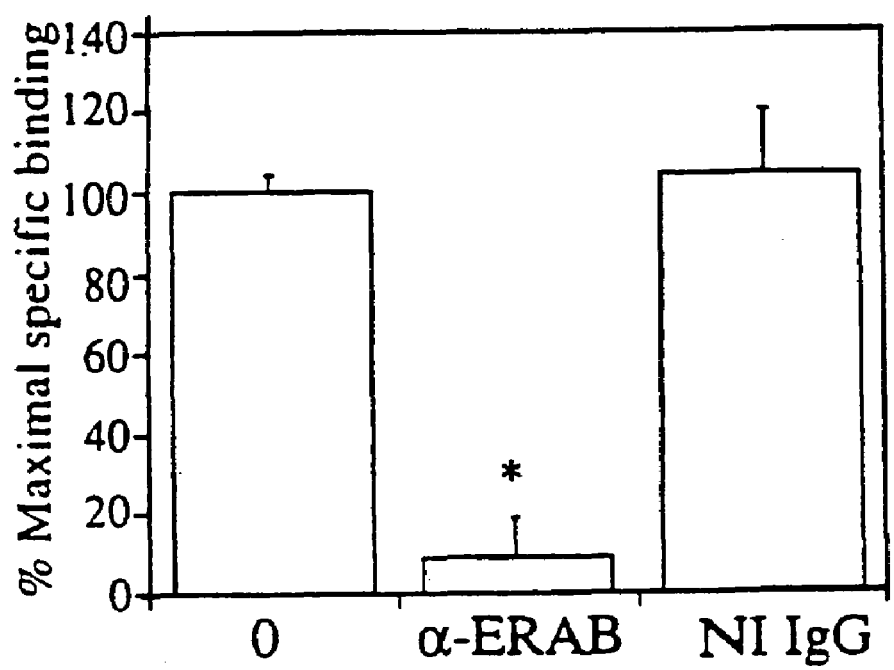
Figure 2D:
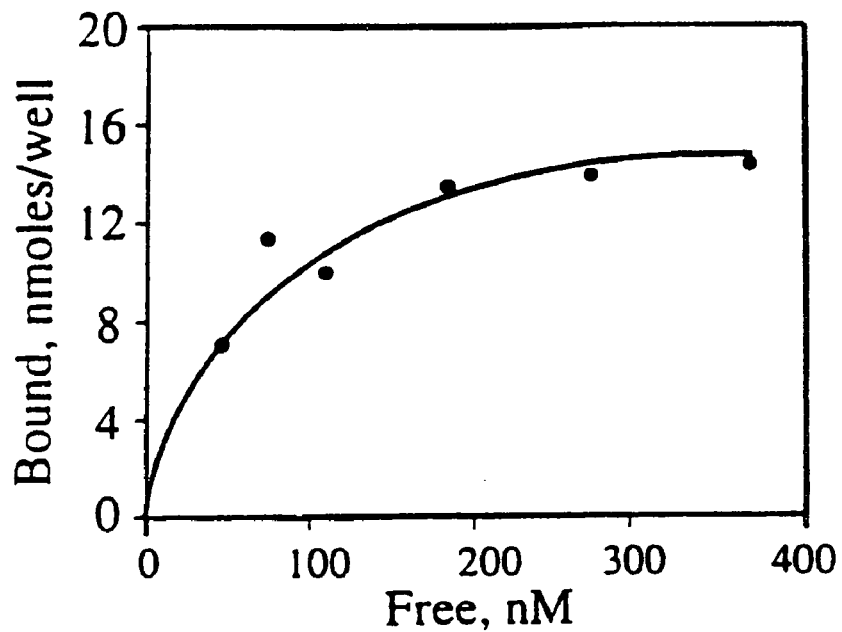
Figure 2E:
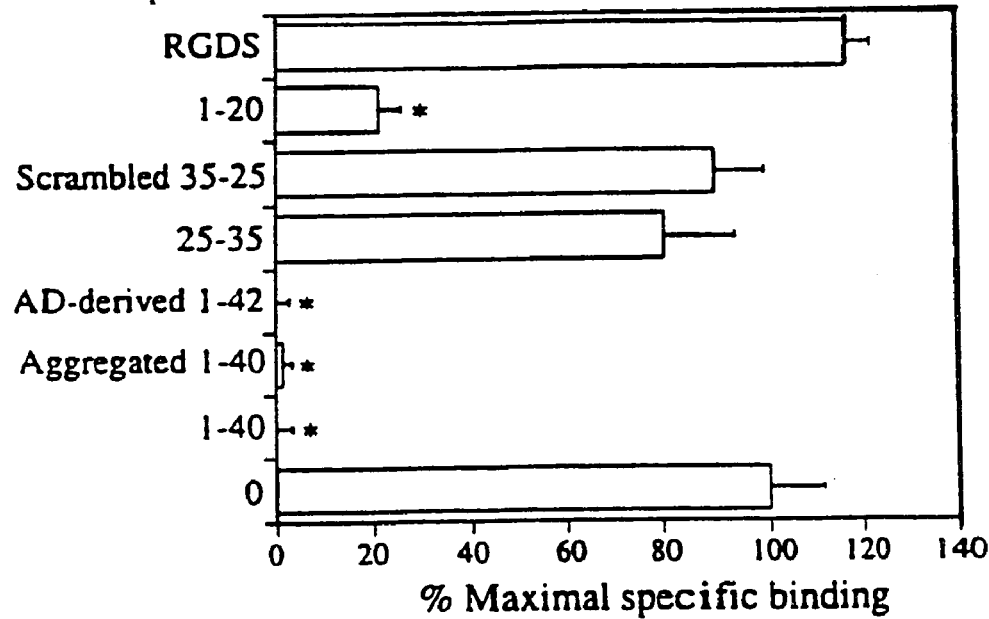
Figure 2F:
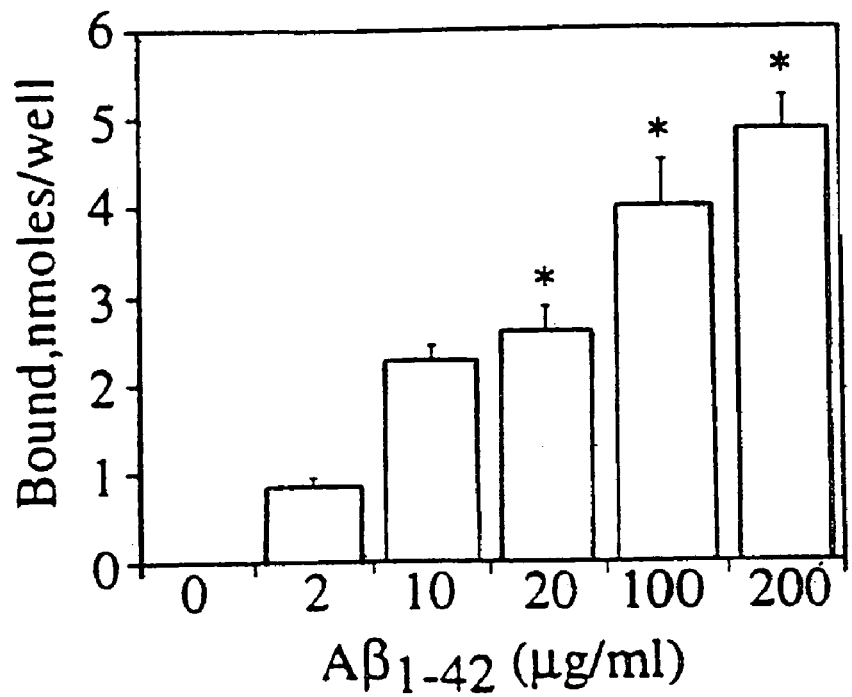
Figure 2G:
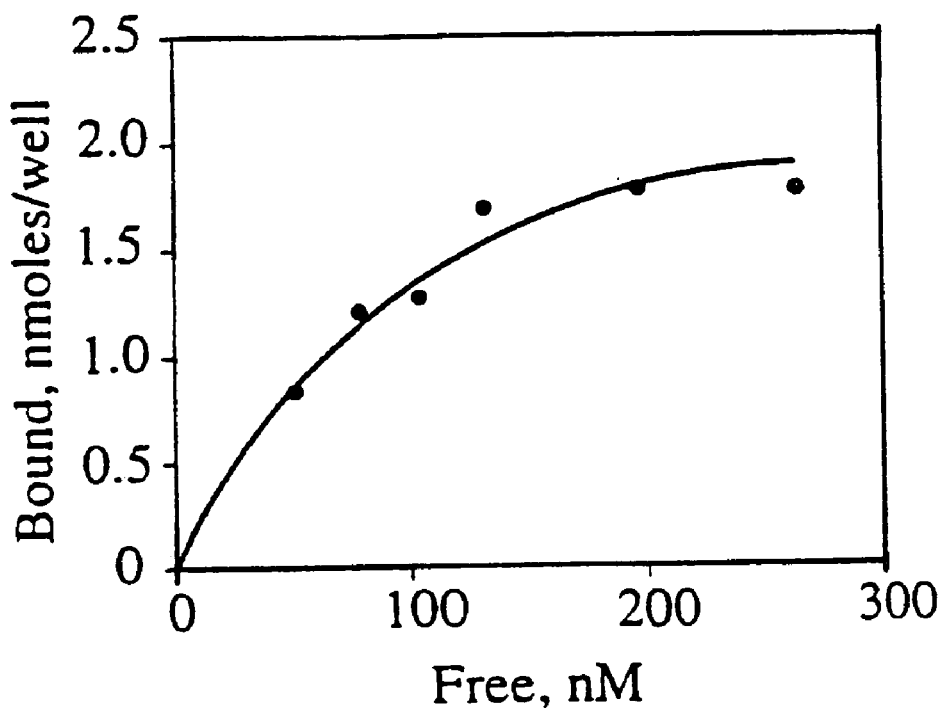
Figure 3A:
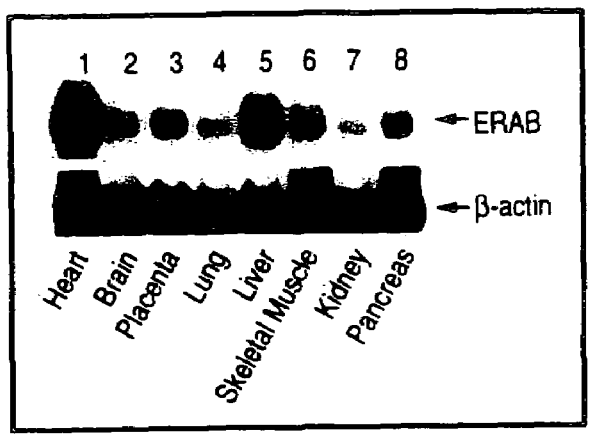
Figure 3B:
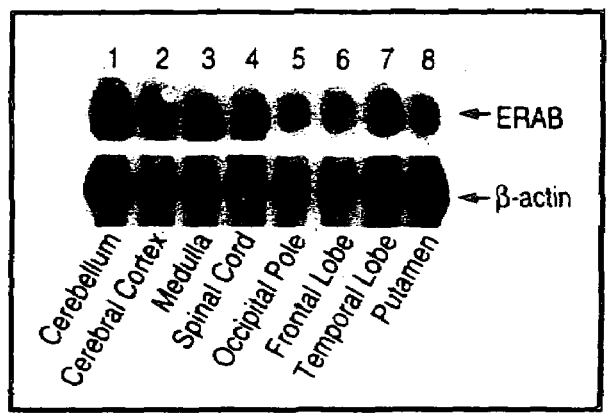
Figure 3C:
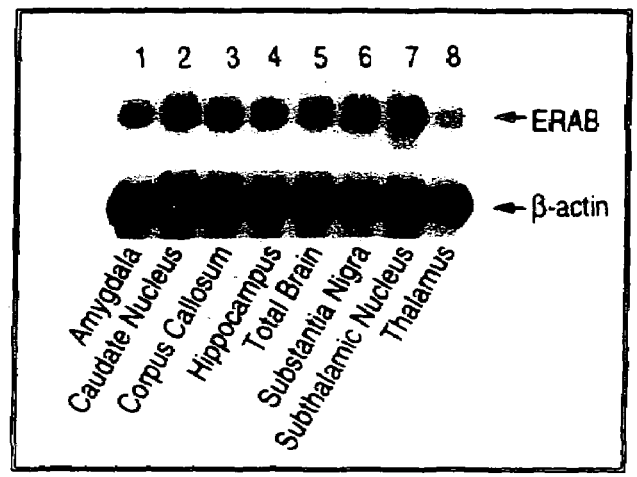

FIGS. 3A, 3B, 3C, 3D, 3E, 3F-1 and 3F-2. Expression of ERAB polypeptide in human tissue. FIGS. 3A, 3B, and 3C. Northern analysis of total RNA harvested from the indicated normal organs (FIG. 3A) or brain subregions (FIGS. 3B and 3C; Clontech) hybridized with full-length $^{32}$P-labelled human cDNA encoding for ERAB polypeptide. Controls were performed by hybridizing the same blots with $^{32}$P-labelled cDNA for β-actin. FIG. 3D. Immunoblotting of brain extracts with anti-ERAB polypeptide IgG. Extracts of human brain temporal lobe were prepared as described (19) and subjected to SDS-PAGE (12%; reduced; 100 µg protein/lane) and immunoblotting. Blots were reacted with rabbit anti-ERAB polypeptide IgG (3 µg/ml) and sites of IgG binding were detected by the chemiluminescence method (Amersham®). In FIG. 3D, lanes 1–2 (designated AD) and FIG. 3D, lanes 3–4 (designated C), extracts were prepared from temporal lobes of two different AD and age-matched normal brains, respectively. FIG. 3D lanes 5–6 show the same samples as in FIG. 3D lanes 1–2, but excess TrcHis-ERAB polypeptide fusion protein was present (20 µg/ml). FIGS. 3E, 3F-1 and 3F-2. Immunostaining for ERAB polypeptide in age-matched normal (FIG. 3E) and AD (FIG. 3F) brain. Brains, obtained within 8 hrs of expiration of the patients, were fixed in paraformaldehyde (4%), paraffin-embedded, sectioned and stained with anti-ERAB polypeptide IgG (30 µg/ml). FIGS. 3F-2 shows double staining displaying amyloid-beta peptide (black) (19) and ERAB polypeptide (red), and was performed as described (19). Scale bar: FIGS. 3E and 3F-1=31 µm; FIGS. 3F-2=25 µm.

Figure 4H:
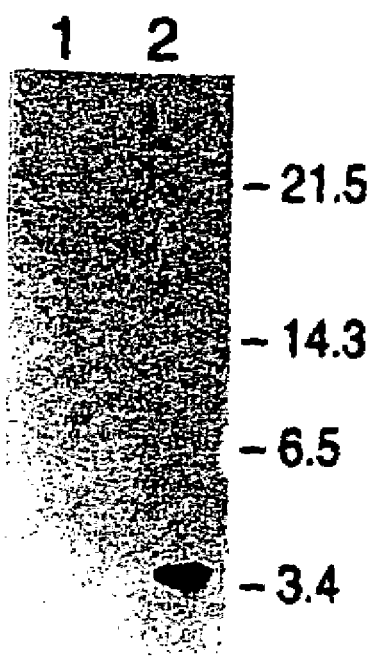
Figure 4I:
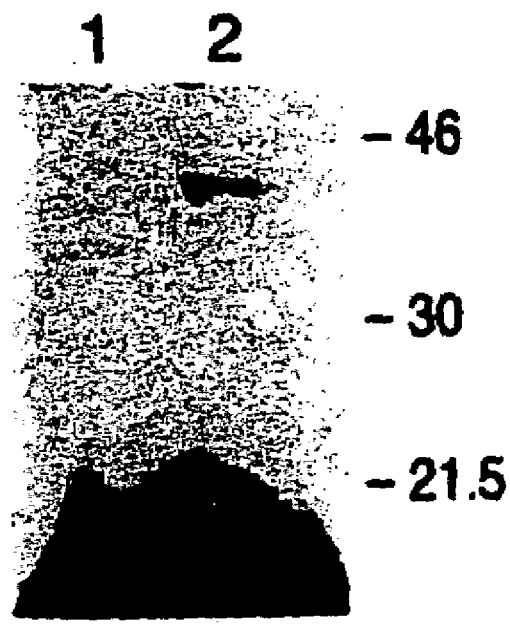

FIGS. 4A, 4B, 4C, 4D, 4E, 4F, 4G, 4H, and 4I. Expression of ERAB polypeptide in cultured cells: localization to the endoplasmic reticulum and change in distribution following addition of amyloid-beta peptide. FIG. 4A. Immunoblotting of ERAB polypeptide in human neuroblastoma SK-N-SH (FIG. 4A, lane 1) and HeLa (FIG. 4A, lane 2) cells. Cell extracts (50 µg protein/lane) were subjected to immunoblotting using anti-ERAB polypeptide IgG (3 µg/ml). FIGS. 4B, 4C, and 4D. Confocal microscopy demonstrating immuno-fluorescence staining for ERAB polypeptide alone (FIG. 4B; red), protein disulfide isomerase alone (FIG. 4C; green), or simultaneous colocalization of these two antigens (FIG. 4D). Scale bar=25 µm. FIG. 4E. Subcellular fractionation of ERAB nucleic acid-transfected human neuroblastoma cells. Transfected cells ($5 \times 10^8$) were pelletted and fractionated in a series of sucrose steps (38%, 30% and 20%) by ultracentrifugation (100,000 for 3 hrs). Layered (FIG. 4E lanes 1–4) and pelletted fractions (FIG. 4E lane 5) were subjected to Western blotting using either anti-ERAB polypeptide IgG (upper panel) or anti-GRP78 IgG (lower panel). Lanes correspond to cytosol (FIG. 4E lane 1), plasma membrane (FIG. 4E lane 2), Golgi apparatus (FIG. 4E lane 3), and endoplasmic reticulum (FIG. 4E lanes 4–5). FIGS. 4F and 4G. Effect of exogenous amyloid-beta peptide (1–42) on ERAB polypeptide distribution. Neuroblastoma cells were incubated in buffer alone or in the presence of amyloid-beta peptide (1–42; 1 $\mu$M), and the distribution of ERAB polypeptide was determined by immunofluorescence with anti-ERAB polypeptide IgG. The antigen becomes localized in packet apparently apposed to plasma membrane. Scale bars E=31 $\mu$m and F=34 $\mu$m. FIGS. 4H and 4I. Co-immunoprecipitation of ERAB polypeptide and amyloid-beta peptide. Neuroblastoma cells ($2 \times 10^7$) were incubated with $^{125}$I-amyloid-beta peptide (100 nM) for 6 hrs at 37° C., unbound tracer was removed by extensive washing followed by dissolution of cells in lysis buffer (19). Immunoprecipitation was performed with anti-ERAB polypeptide IgG (10 $\mu$g/ml; lane 2) or nonimmune IgG (10 $\mu$g/ml; lane 1) and samples were subjected to tris-tricine gel electrophoresis (FIG. 4I). Alternatively, neuroblastoma cells ($2 \times 10^7$) were incubated with $^{125}$I-amyloid-beta peptide (100 nM) for 6 hrs at 37° C., disuccinimidyl suberate (DSS; 0.2 mM; Pierce) was added for 30 min at 25° C., cells were washed extensively to remove free $^{125}$I-amyloid-beta peptide and nonreacted DSS, followed by dissolution of cells in lysis buffer and processing of samples as above (samples were run on nonreduced SDS-PAGE, 10%). In lane 1, immunoprecipitation was performed with nonimmune IgG and in lane 2 anti-ERAB polypeptide IgG was employed. Methods: For indirect immunofluorescence, cells were plated on coverslips, fixed in formaldehyde (3.7%) for 15 min, and permeabilized in Triton X-100 (0.5%) for 5 min. For co-staining, coverslips were sequentially incubated for periods of 1–1.5 hrs at room temperature with monoclonal anti-protein disulfide isomerase (StressGen), anti-mouse FITC (Pierce), rabbit anti-ERAB polypeptide IgG and anti-rabbit TRITC IgG (Pierce). Samples were visualized on a Leica TCS confocal microscope. For subcellular fractionation studies, human neuroblastoma cells were transfected with pcDNA3-ERAB polypeptide encoding vector using the lipofectamine method (19), and fractionated as described following freeze thawing, nitrogen cavitation, homogenization and ultracentrifugation (63).

Figure 5A:
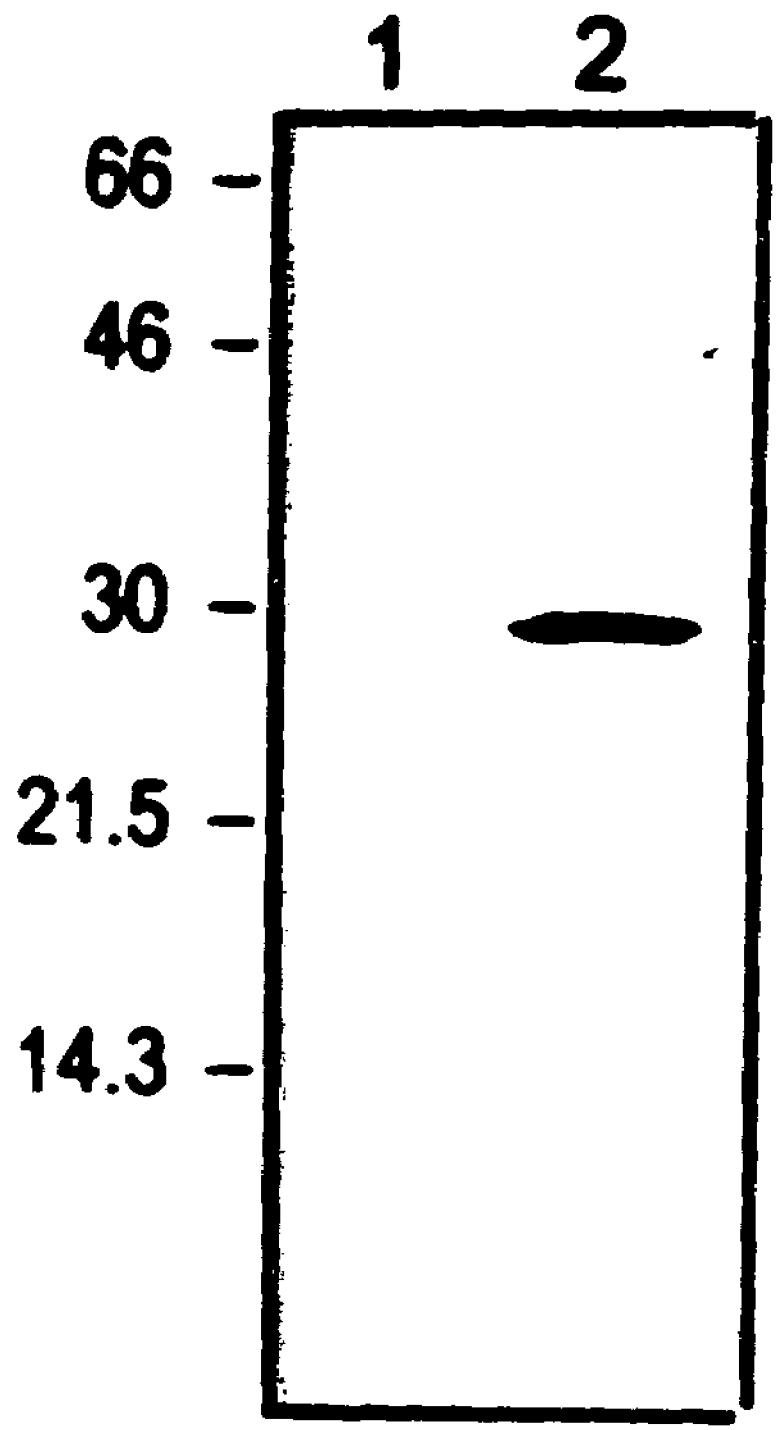
Figure 5B:
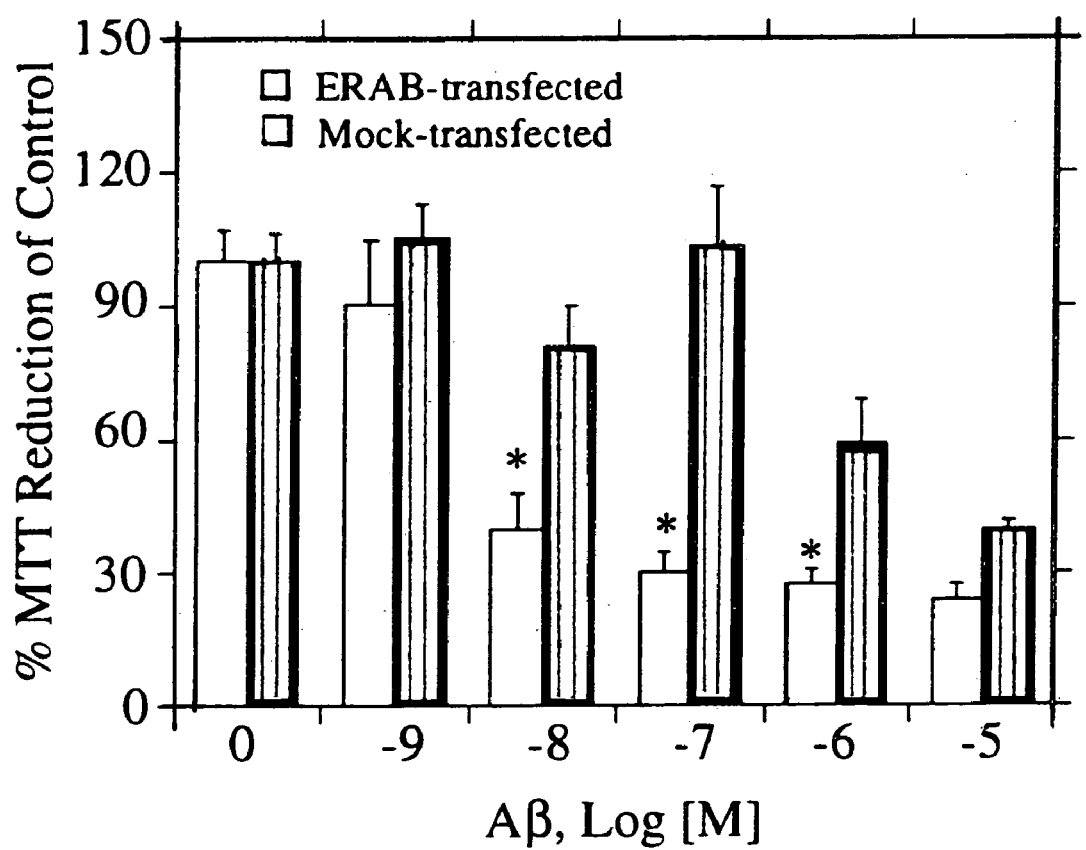

FIGS. 5A, 5B, 5C, 5D, 5E, and 5F. ERAB polypeptide contributes to amyloid-beta peptide-induced cellular toxicity in ERAB nucleic acid-transfected COS cells. FIG. 5A. Immunoblotting of mock-transfected (FIG. 54 lane 1) or ERAB nucleic acid-transfected COS cells (FIG. 5A lane 2; in each case 50 $\mu$g protein/lane was loaded) using anti-ERAB polypeptide IgG (3 $\mu$g/ml). Protein extracts were subjected to SDS-PAGE (12%; reduced) followed by immunoblotting as described above. FIG. 5B. ERAB nucleic acid-transfected COS cells displayed enhanced suppression of MTT reduction in the presence of amyloid-beta peptide. COS cells were transiently transfected with the pcDNA3-ERAB vector or pcDNA3 alone, and, 24 hrs later (at which time ERAB polypeptide is expressed at high levels), amyloid-beta peptide (2 $\mu$M) was added for 24 hrs at 37° C. Then, MTT reduction was determined (36); the mean±SEM of six replicate determinations is shown. * indicates p<0.05. FIGS. 5C, 5D, 5E, and 5F. COS cells were transfected with either vector alone (FIG. 5C), pcDNA3-ERAB vector (FIG. 5D) or pcDNA3-amyloid-beta peptide (1–42; FIG. 5E), or were co-transfected with pcDNA3-ERAB vector and pcDNA3-amyloid-beta peptide (1–42) vectors (FIG. 5F). Overexpression of ERAB polypeptide and/or amyloid-beta peptide was observed in each case, and cultures were photographed at that time. Marker bar=138 $\mu$m. Methods: Transfection was achieved using pcDNA3 vectors bearing either the cDNA for ERAB polypeptide and/or amyloid-beta peptide (A4 corresponding to residues 1–42) using lipofectamine according to the manufacturer's instructions. Maximal cellular expression of ERAB polypeptide and amyloid-beta peptide was observed 24–72 hrs later. MTT reduction was performed and photomicrographs obtained as described (19, 36).

Figure 6C:
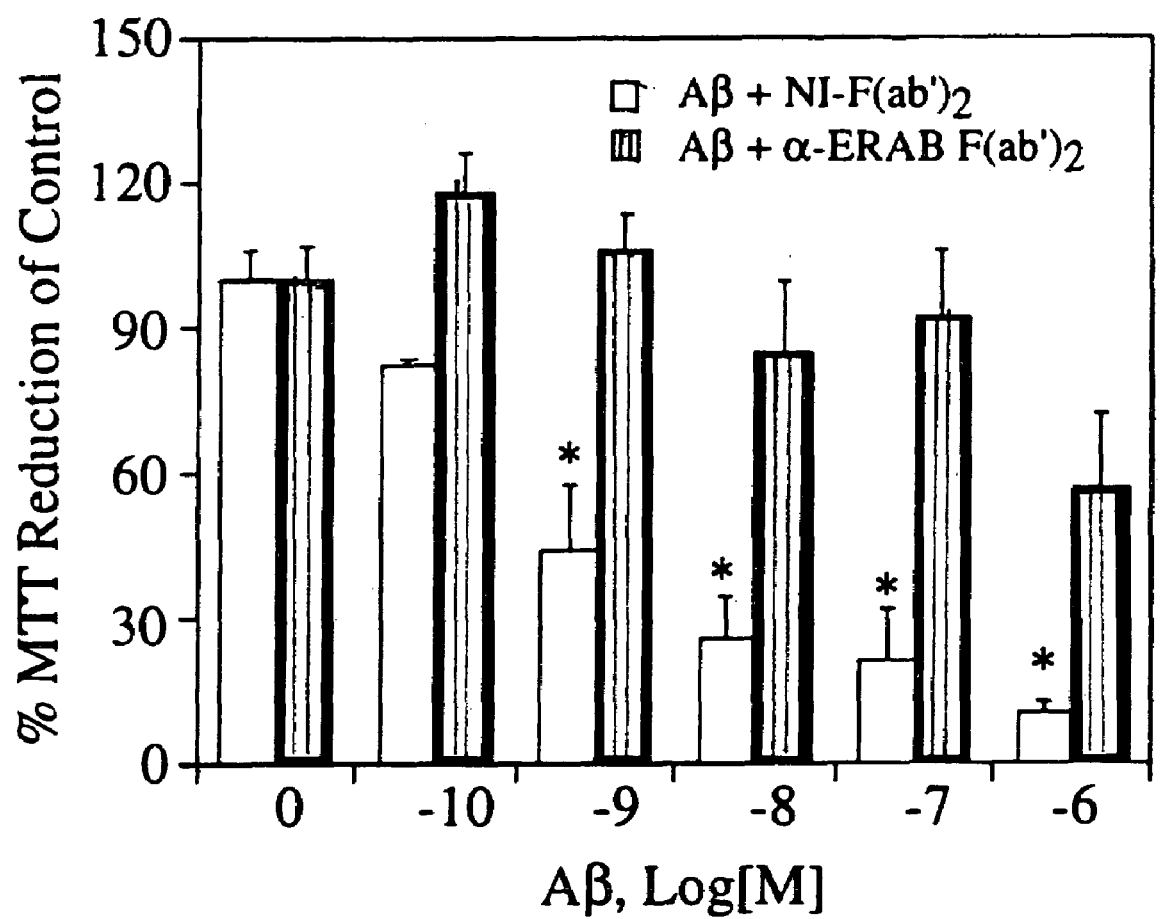

FIGS. 6A, 6B, 6C, 6D, 6E, 6F, and 6G. ERAB polypeptide contributes to amyloid-beta peptide-induced cytotoxicity in neuroblastoma cells. A-B. Introduction of anti-ERAB polypeptide and nonimmune F(ab')$_2$ into neuroblastoma cells (SK-N-SH). F(ab')$_2$ fragments derived from either anti-ERAB polypeptide IgG (FIG. 6A; prepared according to the manufacturer's instructions; Pierce) or nonimmune IgG (FIG. 6B; 13 $\mu$g in each case) were introduced into neuroblastoma cells using lipofectamine as described (65). Immunostaining demonstrates cellular association of the F(ab')$_2$ fragments in each case. Scale bar=18 $\mu$m. FIG. 6C. Effect of anti-ERAB polypeptide F(ab')$_2$ on amyloid-beta peptide-induced suppression of MTT reduction. Anti-ERAB polypeptide or nonimmune F(ab')$_2$ was introduced into SK-N-SH cells as above, and, 24 hrs later, cultures were incubated with the indicated concentrations of amyloid-beta peptide for 20 hrs at 37° C. The mean±SEM of six replicates is shown. * indicates p<0.05. FIGS. 6D, 6E, 6F, and 6G. Effect of anti-ERAB polypeptide F(ab')$_2$ on amyloid-beta peptide-induced morphologic changes. Anti-ERAB polypeptide or nonimmune F(ab')$_2$ was introduced into SK-N-SH cells, cultures were incubated with amyloid-beta peptide (1–42; 1 $\mu$M), and were then photographed: FIG. 6D, untreated cultures; FIG. 6E, cultures exposed to amyloid-beta peptide; FIG. 6F, cultures into which anti-ERAB polypeptide F(ab')$_2$ was introduced using liposomes then exposed to amyloid-beta peptide; and FIG. 6G, cultures into which nonimmune F(ab')$_2$ was introduced using liposomes then exposed to amyloid-beta peptide. Scale bar=138 $\mu$m.

Figure 7:
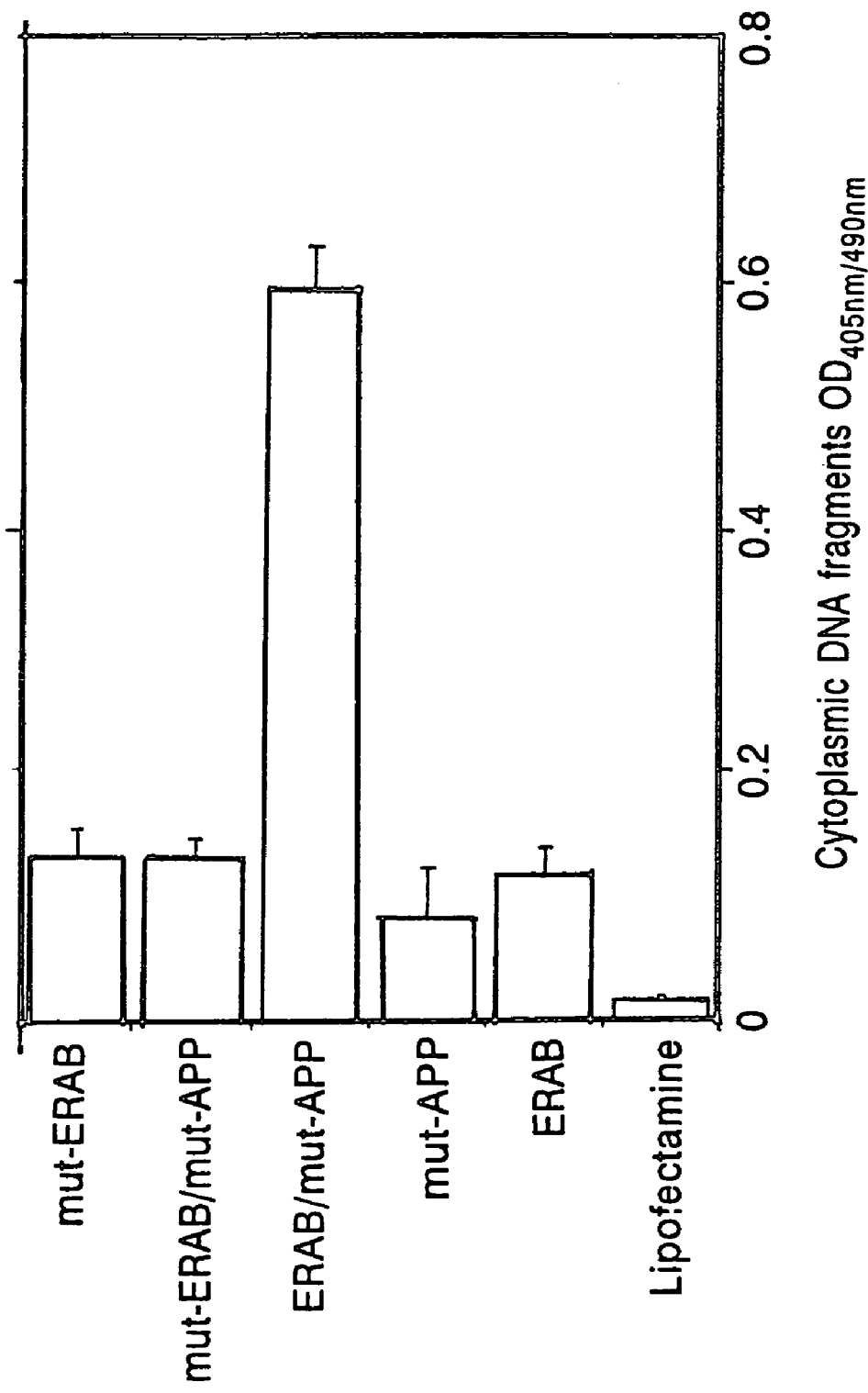

FIG. 7. Overexpression of a mutant form of beta-amyloid precursor protein ($\beta$APP) which causes increased expression of amyloid-beta protein ($\beta$A), and ERAB causes increased toxicity (DNA fragmentation) to COS cells.

DETAILED DESCRIPTION

As used herein, a polypeptide is an amino acid polymer of amino acids linked together by peptide bonds; a nucleic acid is a deoxyribonucleotide or ribonucleotide polymer of nucleotides linked together by phosphodiester bonds; an antisense nucleic acid is a nucleic acid that is the reverse complement of another nucleic acid which may be capable of inhibiting transcription or translation of the other nucleic acid; a vector is a nucleic acid that can self replicate; a host cell is a cell containing a vector; an antibody is a protein with a specific affinity for an antigen; an antibody binding fragment (F(ab)) is a portion of an antibody which binds to the antigen; and a transgenic animal is an animal whose cells comprise a foreign nucleic acid or naturally occurring nucleic acid in unnatural quantities or frequency (84).

As used herein, the term "ERAB" is an abbreviation for "endoplasmic reticulum associated amyloid-beta peptide binding." The term "ERAB polypeptide" refers to an endoplasmic reticulum associated amyloid-beta binding polypeptide. ERAB polypeptide has a biological activity characterized by the capability of binding to amyloid-beta peptide. ERAB polypeptide is also characterized by hydroxysteroid dehydrogenase activity. The term "ERAB nucleic acid" refers to a nucleic acid encoding ERAB polypeptide. The term "ERAB antisense nucleic acid" refers to the noncoding nucleic acid corresponding to an ERAB nucleic acid. The term "ERAB antibody" refers to an antibody to the antigen "ERAB polypeptide." The term "ERAB antibody F(ab)" refers to the antigen binding fragment of an ERAB antibody.

This invention provides an ERAB polypeptide. In an embodiment, the ERAB polypeptide has a theoretical weight of about 27,000 daltons. In another embodiment, the ERAB polypeptide has an SDS-PAGE-determined weight of about 29,000 daltons. One embodiment of an ERAB polypeptide is human ERAB polypeptide or a murine ERAB polypeptide. In a specific embodiment a human ERAB polypeptide has the amino acid sequence shown in FIG. 1D (Seq. Id. No. 2). Another embodiment may be a portion of the ERAB polypeptide amino acid sequence shown in FIG. 1D (Seq. Id. No. 2).

The present invention includes variants of ERAB polypeptide which encompass proteins and peptides with amino acid sequences having seventy percent or eighty percent homology with the amino acid sequence shown in FIG. 1D (Seq. Id. No. 2) or a naturally occurring ERAB polypeptide. More preferably the sequence homology is at least ninety percent, or at least ninety-five percent.

Variants in amino acid sequence of ERAB polypeptide are produced when one or more amino acids in naturally occurring ERAB polypeptide is substituted with a different natural amino acid, an amino acid derivative, a synthetic amino acid, an amino acid analog or a non-native amino acid. Particularly preferred variants include homologous ERAB polypeptide of humans or of different species of animals. Variants of an ERAB polypeptide may include biologically active fragments of naturally occurring ERAB polypeptide, wherein sequences of the variant differ from the wild type ERAS polypeptide sequence by one or more conservative amino acid substitutions. Such substitutions typically would have minimal influence on the secondary structure and hydrophobic nature of the ERAB polypeptide. Variants may also have sequences which differ by one or more non-conservative amino acid substitutions, deletions or insertions which do not abolish the biological activity associated with ERAB polypeptide. Conservative substitutions (substituents) typically include the substitution of one amino acid for another with similar characteristics such as substitutions within the following groups: valine, glycine; glycine, alanine; valine, isoleucine; aspartic acid, glutamic acid; asparagine, glutamine; serine, threonine; lysine, arginine; and phenylalanine, tyrosine. The non-polar (hydrophobic) amino acids include alanine, leucine, isoleucine, valine, praline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid.

Other conservative substitutions are exemplified Table 1, and yet others are described by Dayhoff in the *Atlas of Protein Sequence and Structure* (1988) (86).

TABLE 1

Conservative Amino Acid Replacements

| For Amino Acid | Code | Replace with any of |
|---|---|---|
| Alanine | A | D-Ala, Gly, beta-ALa, L-Cys, D-Cys |
| Arginine | R | D-Arg, Lys, homo-Arg, D-homo-Arg, Met, D-Met, Ile, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S—Me—Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, Beta-Ala, Acp |
| Isoleucine | I | D-Ile, Val, D-Val, Leu, D-Leu, Met, D-Met |
| Leucine | L | D-Leu, Val, D-Val, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S—Me—Cys, Ile, D-Ile, Leu, D-Leu, Val, D-Val, Norleu |
| Phenylalanine | F | D-Phe, Tyr, D-Thr, L-Dopa, His, D-His, Trp, D-Trp, Trans 3,4 or 5-phenylproline, cis 3,4 or 5 phenylproline |
| Proline | P | D-Pro, L-I-thioazolidine-4-carboxylic acid, D- or L-1-oxazolidine-4-carboxylic acid |
| Serine | S | D-Ser, Thr, D-Thr, allo-Thr, Met, D-Met, Met(O), D-Met(O), Val, D-Val |
| Threonine | T | D-Thr, Ser, D-Ser, allo-Thr, Met, D-Met, Met(O) D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

Other variants within the invention are those with modifications which increase peptide stability. Such variants may contain, for example, one or more non-peptide bonds (which replace the peptide bonds) in the peptide sequence. Also included are: variants that include residues other than naturally occurring L-amino acids, such as D-amino acids or non-naturally occurring or synthetic amino acids such as beta or gamma amino acids. Incorporation of D- instead of L-amino acids into the polypeptide may increase its resistance to proteases. See, e.g., U.S. Pat. No. 5,219,990 (87).

An ERAB polypeptide variant of this invention includes an ERAB polypeptide varied by changes such as insertions, deletions and substitutions, either conservative or nonconservative where such changes might provide for certain advantages in their use such as increased potency, bioavailability, stability or decreased toxicity or degradation under physiological conditions.

In other embodiments, variants with amino acid substitutions which are less conservative may also result in desired derivatives of ERAS polypeptide, e.g., by causing desireable changes in charge, conformation and other biological properties. Such substitutions would include for example, substitution of hydrophilic residue for a hydrophobic residue, substitution of a cysteine or proline for another residue, substitution of a residue having a small side chain for a residue having a bulky side chain or substitution of a residue having a net positive charge for a residue having a net negative charge. When the result of a given substitution cannot be predicted with certainty, the derivatives may be readily assayed according to the methods disclosed herein to determine the presence or absence of the desired characteristics.

Just as it is possible to replace substituents of the scaffold (i.e., amino acids which make up the ERAB polypeptide), it is also possible to substitute functional groups which decorate the scaffold with groups characterized by similar features (i.e., R-groups which are part of each amino acid). These substitutions will initially be conservative, i.e., the replacement group will have approximately the same size, shape, hydrophobicity and charge as the original group. Non-sequence modifications may include, for example, in vivo or in vitro chemical derivatization of portions of naturally occurring ERAB polypeptide, as well as changes in acetylation, methylation, phosphorylation, carboxylation or glycosylation.

In a further embodiment the ERAB polypeptide is modified by chemical modifications in which activity is preserved. For example, the ERAB polypeptide may be amidated, sulfated, singly or multiply halogenated, alkylated, carboxylated, or phosphorylated. The ERAB polypeptide may also be singly or multiply acylated, such as with an acetyl group, with a farnesyl moiety, or with a fatty acid, which may be saturated, monounsaturated or polyunsaturated. The fatty acid may also be singly or multiply fluorinated. The invention also includes methionine analogs of ERAB polypeptide, for example the methionine sulfone and methionine sulfoxide analogs. The invention also includes salts of ERAB polypeptide, such as ammonium salts, including alkyl or aryl ammonium salts, sulfate, hydrogen sulfate, phosphate, hydrogen phosphate, dihydrogen phosphate, thiosulfate, carbonate, bicarbonate, benzoate, sulfonate, thiosulfonate, mesylate, ethyl sulfonate and benzensulfonate salts.

Variants of ERAB polypeptide may also include peptidomimetic compounds of ERAB polypeptide. Such compounds are well known to those of skill in the art and are produced through the substitution of certain R groups or amino acids in the protein with non-natural replacements. Such substitutions may increase the stability, bioavailability, or activity of such ERAB polypeptide compound.

The present invention provides an ERAB nucleic acid. One embodiment of an ERAB nucleic acid is a recombinant ERAB nucleic acid. A further embodiment of an ERAB nucleic acid is human. ERAB nucleic acid. An embodiment of an ERAB nucleic acid is an ERAB deoxyribonucleic acid (DNA), a recombinant nucleic acid, or an ERAS ribonucleic acid. A specific embodiment of human ERAB nucleic acid is a cDNA sequence which corresponds to the sequence shown in FIG. 1D from nucleotide 19 to nucleotide 801 or a portion thereof. One embodiment of the present invention is murine ERAB nucleic acid.

The invention also provides variants of the ERAB nucleic acid. Variants of ERAB nucleic acid may include nucleic acid sequences having seventy percent or eighty percent homology with the ERAB nucleic acid sequence shown in FIG. 1D. More preferably the sequence homology is at least ninety percent, or at least ninety-five percent. Variants of ERAB nucleic acid may include alleles of ERAB nucleic acid, truncated ERAB nucleic acid, alternatively spliced ERAB nucleic acid, ERAB nucleic acid with silent mutations or conservative mutations. A variant of ERAB nucleic acid may also include portions of naturally occuring ERAB nucleic acid or ERAB nucleic acid with deletions of some regions of the nucleic acid.

The present invention provides an ERAB antisense nucleic acid. In one embodiment, the ERAB antisense nucleic acid is human ERAB antisense nucleic acid or a portion of human ERAB antisense nucleic acid. In a further embodiment, the human ERAB antisense nucleic acid sequence in the 3' to 5' direction corresponds to the nucleic acid sequence shown in FIG. 1D in the 5' to 3' direction.

The antisense nucleic acid may be capable of inhibiting translation or transcription of an ERAB nucleic acid or an mRNA derived from an ERAB nucleic acid. The antisense sequence to ERAB nucleic acid may be linked to a replicable vector. The ERAB antisense nucleic acid may be administered to a subject in order to treat a neurodegenerative condition. The ERAB antisense nucleic acid may inhibit the binding of an ERAB polypeptide in a cell to amyloid-beta peptide.

The present invention provides for a replicable vector containing an ERAB nucleic acid or a variant thereof. In one embodiment the vector is a prokaryotic expression vector, a yeast expression vector, a baculovirus expression, a mammalian expression vector, an episomal mammalian expression vector, pKK233-2, pEUK-Cl, pREP4, pBlueBacHis A, pYES2, pSE280, or pEBVHis. Methods for the using these replicable vectors may be found in Sambrook et al., 1989, (79) or Kriegler, 1990, (88).

The present invention provides for an host cells comprising an ERAB nucleic acid or variant thereof. In one embodiment the host cell is a eukaryotic cell, a somatic cell, a germ cell, a neuronal cell, a myocyte, a prokaryotic cell, a virus packaging cell, or a stem cell.

This invention provides the production of biologically active ERAB polypeptide in a prokaryotic expression system, a eukaryotic expression system, a mammalian expression system, a baculovirus expression system, an insect expression system or a yeast expression system. This production may provide for the post-translational modifications which exist in naturally occurring ERAB polypeptide. For protocols describing bacterial expression of mammalian proteins, see Sambrook et al, 1989 (79).

The present invention provides a transgenic animal whose cells express ERAB nucleic acid or a variant thereof. In one embodiment, the cells of the transgenic animal contain human ERAB nucleic acid. In another embodiment the transgenic animal is a non-human mammal. In another embodiment, the non-human mammal is a mouse, monkey, a dog, a swine, a fowl or a rat. In a specific embodiment, the transgenic animal may be a non-human mammal whose germ and somatic cells contain a human ERAB nucleic acid, the nucleic acid having been stably introduced into the non-human mammal at the single cell stage or an embryonic stage, and wherein the nucleic acid is linked to a promoter and integrated into the genome of the non-human mammal. The transgenic animal may be a descendant of an animal containing cells which have been transfected with ERAB nucleic acid or a variant thereof.

The present invention provides an antibody which is an antibody or a portion thereof which specifically binds to an ERAB polypeptide or variant thereof. In one embodiment the antibody is a polyclonal antibody, a monoclonal antibody or an antigen binding fragment (F(ab)) of antibody. In another embodiment, the antibody comprises an antibody which binds to human ERAB polypeptide or to murine ERAB polypeptide or to a portion of the polypeptide shown in FIG. 1D.

One of ordinary skill in the art would know how to make and use such an antibody. The present invention provides for a fragment of an antibody to ERAB polypeptide, namely [F(ab')$_2$] which is capable of blocking the binding activity of ERAB polypeptide to amyloid-beta peptide. Such antibodies may be introduced into cells and may be capable of suppressing the toxicity or cell stress due to amyloid-beta peptide. The antibody may be a small synthetic peptide. The antibody may block the binding of ERAB polypeptide to amyloid-beta peptide by binding to a binding site on an ERAB polypeptide or on an amyloid-beta peptide.

The present invention provides a method to determine the ability of an agent to inhibit binding of ERAB polypeptide to amyloid-beta peptide which comprises: (a) incubating ERAB polypeptide and the agent with amyloid-beta peptide; (b) determining the amount of amyloid-beta peptide bound to ERAB polypeptide; and (c) comparing the determined amount with an amount determined when the agent is absent, thereby determining the ability of the agent to inhibit the binding of ERAB polypeptide to amyloid-beta peptide. The agent may be a peptide, a peptidomimetic compound, a nucleic aced, or a small molecule. In one embodiment, the agent may be marked with a reporter molecule. In another embodiment, the ERAS polypeptide or amyloid-beta peptide may be marked with a reporter molecule.

A "reporter molecule", as defined herein, is a molecule or atom which, by its chemical nature, provides an identifiable signal allowing detection of the level of production of a particular protein, mRNA or transcript. Detection can be either qualitative or quantitative. The present invention provides for the use of any commonly used reporter molecule including radionucleotides, enzymes, biotins, psoralens, fluorophores, chelated heavy metals, and luciferase. The most commonly used reporter molecules are either enzymes, fluorophores, or radionucleotides linked to the nucleotides which are used in transcription. Commonly used enzymes include horseradish peroxidase, alkaline phosphatase, glucose oxidase and α-galactosidase, β-glucuronidase among others. The substrates to be used with the specific enzymes are generally chosen because a detectably colored product is formed by the enzyme acting upon the substrate. For example, p-nitrophenyl phosphate is suitable for use with alkaline phosphatase conjugates; for horseradish peroxidase, 1.2-phenylenediamine, 5-aminosalicylic acid or toluidine are commonly used. The probes so generated have utility in the detection of a specific ERAB nucleic acid target in, for example, Southern analysis, Northern analysis, in situ hybridization to tissue sections or chromosomal squashes and other analytical and diagnostic procedures. The methods of using such hybridization probes are well known and some examples of such methodology are provided by Sambrook et al, 1989 (79). The reporter molecule may be linked to a probe for an ERAB nucleic acid or an ERAB antibody and may be used for prognosis determination in a subject for neurodegenerative conditions.

An example of a model agent which would inhibit the binding of ERAB polypeptide to amyloid-beta peptide includes an F(ab')$_2$ prepared from anti-ERAB polypeptide-derived IgG, IgM, IgE or any other immunoglobulin molecule. The F(ab') fragment of the antibody may be used instead of the whole IgG molecule since it is to be introduced into a cell and the whole antibody would likely have nonspecific effects due to its Fc region. The agent described herein may work when it is introduced into cells. Such introduction may be achieved via liposomes, Lipofectin, calcium precipitation and other methods. Such methods of introducing compounds, protein, nucleic acid and polypeptides into cells are well known to one of ordinary skill in the art.

The present invention also provides assays for the determination or identification of compounds capable of inhibiting the binding of ERAB polypeptide to amyloid-beta peptide. Such an assay may include the binding of radiolabelled $^{125}$I-amyloid-beta peptide or labelled amyloid-beta peptide of any form to ERAB polypeptide. The amyloid-beta peptide or the ERAB polypeptide may be bound to a solid support. The amyloid-beta peptide or the ERAB polypeptide may be a fusion protein. The assay may also detect the binding of amyloid-beta peptide to immobilized ERAB polypeptide. Compounds may be added to the reaction mixture and detection of binding or the inhibition of binding may be determined. Such assays are useful for the identification of compounds which could be used as agents capable of inhibiting the binding of the amyloid-beta peptide with ERAB polypeptide. Such an agent may be used as a drug or a pharmaceutical composition or a preventative drug to ameliorate, prevent, treat or improve neurodegenerative conditions in subjects. The subjects may be humans, animals, mice, dogs, cats or other animals. Such animals may be useful human model systems.

The present invention provides a method to determine the prognosis of a neurodegenerative condition in a subject which comprises: (a) obtaining a sample from the subject; (b) contacting the sample with a reagent capable of binding to an element in the sample, the element comprising ERAB nucleic acid or ERAB polypeptide or variant thereof, under conditions such that the reagent binds only if the element is present in the sample; and (c) detecting the presence of the reagent bound to the element and thereby determining the prognosis of the neurodegenerative condition of the subject.

In an embodiment of this invention the subject is a mammal. Examples of suitable mammalian subjects include, but are not limited to, murine animals such as mice and rats, hamsters, rabbits, goats, pigs, sheep, cats, dogs, cows, monkeys and humans.

The present invention further provides a method to treat or cure a neurodegenerative condition in a subject which comprises administering to the subject a pharmaceutically acceptable composition, such composition comprising an agent capable of inhibiting the interaction or binding of ERAB polypeptide with amyloid-beta peptide in the subject, in an amount effective to treat or cure the neurodegenerative condition in the subject.

The agent or compound determined or identified by the above assays or methods may be used as a drug or in a pharmaceutical composition. Such drug or pharmaceutical composition may be administered to subjects suffering from a neurodegenerative condition. The administration times, concentrations, and duration would be known by one of ordinary skill in the art and would depend on a number of discernable factors including the body weight of the subject, the type of the neurodegenerative condition, the stage of the condition, the age of the subject, the health of the subject, among other factors.

The present invention provides a pharmaceutical composition which comprises an agent capable of inhibiting binding of amyloid-beta peptide to ERAB polypeptide and a pharmaceutically acceptable carrier thereof. The carrier may be a diluent, an aerosol, a topical carrier, an aqueous solution, a nonaqueous solution or a solid carrier.

In the practice of any of the methods of the invention or preparation of any of the pharmaceutical compositions, a "therapeutically effective amount" is an amount which is effective to alter the binding of ERAB polypeptide to amyloid-beta peptide and thus treat the neurodegenerative condition of the subject. Accordingly, the effective amount will vary with the subject being treated, as well as the condition to be treated. For the purposes of this invention, the methods of administration are to include, but are not limited to, administration cutaneously, subcutaneously, intravenously, parenterally, orally, topically, or by aerosol.

As used herein, the term "suitable pharmaceutically acceptable carrier" encompasses any of the standard pharmaceutically accepted carriers, such as phosphate buffered saline solution, water, emulsions such as an oil/water emulsion or a triglyceride emulsion, various types of wetting agents, tablets, coated tablets and capsules. An example of an acceptable triglyceride emulsion useful in intravenous and intraperitoneal administration of the compounds is the triglyceride emulsion commercially known as Intralipid®.

Typically such carriers contain excipients such as starch, milk, sugar, certain types of clay, gelatin, stearic acid, talc, vegetable fats or oils, gums, glycols, or other known excipients. Such carriers may also include flavor and color additives or other ingredients.

By means of well-known techniques such as titration and by taking into account the observed pharmacokinetic characteristics of the agent in the individual subject, one of skill in the art can determine an appropriate dosing regimen (85).

The present invention further provides for a method for treating a neurodegenerative condition in a subject which comprises administering to the subject an amount of an agent effective to inhibit ERAB binding to amyloid-beta peptide thereby treating the neurodegenerative condition.

The neurodegenerative condition may comprise Alzheimer's disease, Down's syndrome, Parkinson's disease, Huntington's disease, schizophrenia, multiple sclerosis, senility, stroke, demyelinating disease, or a heritable condition.

As used herein, the term "neurotoxicity" encompasses the negative metabolic, biochemical and physiological effects on a neuronal cell which may result in a debilitation of the neuronal cellular functions. Such functions may include memory, learning, perception, neuronal electrophysiology (ie. action potentials, polarizations and synapses), synapse formation, both chemical and electrical, channel functions, neurotransmitter release and detection and neuromotor functions. Neurotoxicity may include neuronal cytotoxicity.

As used herein, the term "neuronal degeneration" encompasses a decline in normal functioning of a neuronal cell. Such a decline may include a decline in memory, learning, perception, neuronal electrophysiology (ie. action potentials, polarizations and synapses), synapse formation, both chemical and electrical, channel functions, neurotransmitter release and detection and neuromotor functions. In the present invention, the subject may be a mammal or a human subject. The administration may be intralesional, intraperitoneal, intramuscular or intravenous injection; infusion; liposome-mediated delivery; gene bombardment; topical, nasal, oral, anal, ocular or otic delivery.

The present invention provides for a pharmaceutical composition which comprises an antibody specific for ERAB polypeptide and a pharmaceutically acceptable carrier thereof. The present invention also provides for a pharmaceutical composition which comprises an antisense nucleic acid corresponding to ERAB nucleic acid or a variant thereof and a pharmaceutically acceptable carrier thereof. The present invention provides for a pharmaceutical composition which comprises a portion of an ERAB polypeptide sufficient to inhibit binding of ERAB polypeptide to amyloid-beta peptide in a cell and a pharmaceutically acceptable carrier.

Also provided by the invention are pharmaceutical compositions comprising therapeutically effective amounts of products of the invention together with suitable diluents, preservatives, solubilizers, emulsifiers, adjuvants and/or carriers. A "therapeutically effective amount" as used herein refers to that amount which provides a therapeutic effect for a given condition and administration regimen. [One example would be a sufficient amount to treat or ameliorate a neurodegenerative condition in a subject, such as Alzheimer's Disease.] Such compositions are liquids or lyophilized or otherwise dried formulations and include diluents of various buffer content (e.g., Tris-HCl, acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polyglycolic acid, hydrogels, etc, or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance. The choice of compositions will depend on the physical and chemical properties of the exact protein or compound having the activity of inhibiting the neurdegenerative condition. For example, a product derived from a membrane-bound form of a protein may require a formulation containing detergent.

Controlled or sustained release compositions include formulation in lipophilic depots (e.g., fatty acids, waxes, oils). Also comprehended by the invention are particulate compositions coated with polymers (e.g., poloxamers or poloxamines) and the compound coupled to antibodies directed against tissue-specific receptors, ligands or antigens or coupled to ligands of tissue-specific receptors. Other embodiments of the compositions of the invention incorporate particulate forms protective coatings, protease inhibitors or permeation enhancers for various routes of administration, including parenteral, pulmonary, nasal, oral, injection or infusion by intravenous, intraperitoneal, intracerebral, intramuscular, intraocular, intraarterial or intralesional.

Another embodiment of this invention is a method for evaluating the ability of an agent to inhibit binding of an amyloid-beta peptide with an ERAB polypeptide in a cell which includes: a) contacting the cell with the agent; b) determining the amount of amyloid-beta peptide bound to ERAB polypeptide in the cell; and c) comparing the amount of bound amyloid-beta peptide to ERAB polypeptide determined in step b) with the amount determined in the absence of the agent, thus evaluating the ability of the agent to inhibit the binding of amyloid-beta peptide to ERAB polypeptide in the cell.

The agent may be capable of specifically binding to the amyloid-beta peptide or to ERAB polypeptide. The agent may bind to amyloid-beta peptide at the site where ERAB polypeptide interacts. The agent may be a soluble portion of an ERAB polypeptide which is not associated with a cell membrane. The agent may be bound to a solid support. The agent may be expressed on the surface of a cell or may be produced inside of the cell.

Portions of the compound of the invention may be "labeled" by association with a detectable marker substance (e.g. radiolabeled with $^{125}$I or biotinylated) to provide reagents useful in detecting and quantifying the presence of ERAB polypeptide or ERAB nucleic acid or their derivatives in solid tissue and fluid samples such as blood, cerebral spinal fluid or urine.

When administered, agents are often cleared rapidly from the circulation and may therefore elicit relatively short-lived pharmacological activity. Consequently, frequent injections of relatively large doses of bioactive agents may by required to sustain therapeutic efficacy. Agents modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified agents (80, 82, 83). Such modifications may also increase the agent's solubility in aqueous solution, eliminate aggregation, enhance the physical and chemical stability of the agent, and greatly reduce the immunogenicity and reactivity of the agent. As a result, the desired in vivo biological activity may be achieved by the administration of such polymer-agent adducts less frequently or in lower doses than with the unmodified agent.

Attachment of polyethylene glycol (PEG) to agents or compounds is particularly useful because PEG has very low toxicity in mammals (81). For example, a PEG adduce of adenosine deaminase was approved in the United States for use in humans for the treatment of severe combined immunodeficiency syndrome. A second advantage afforded by the conjugation of PEG is that of effectively reducing the immunogenicity and antigenicity of heterologous compounds. For example, a PEG adduct of a human protein might be useful for the treatment of disease in other mammalian species without the risk of triggering a severe immune response. The agent may be delivered in a microencapsulation device so as to reduce or prevent an host immune response against the agent or against cells which may produce the agent. The agent of the present invention may also be delivered microencapsulated in a membrane, such as a liposome.

Polymers such as PEG may be conveniently attached to one or more reactive amino acid residues in a protein such as the alpha-amino group of the amino terminal amino acid, the epsilon amino groups of lysine side chains, the sulfhydryl groups of cysteine side chains, the carboxyl groups of aspartyl and glutamyl side chains, the alpha-carboxyl group of the carboxy-terminal amino acid, tyrosine side chains, or to activated derivatives of glycosyl chains attached to certain asparagine, serine or threonine residues.

Numerous activated forms of PEG suitable for direct reaction with proteins have been described. Useful PEG reagents for reaction with protein amino groups include active esters of carboxylic acid or carbonate derivatives, particularly those in which the leaving groups are N-hydroxysuccinimide, p-nitrophenol, imidazole or 1-hydroxy-2-nitrobenzene-4-sulfonate. PEG derivatives containing maleimido or haloacetyl groups are useful reagents for the modification of protein free sulfhydryl groups. Likewise, PEG reagents containing amino hydrazine or hydrazide groups are useful for reaction with aldehydes generated by periodate oxidation of carbohydrate groups in proteins.

The present invention incorporates U.S. Pat. Nos. 5,446,128, 5,422,426 and 5,440,013 in their entireties as references which disclose the synthesis of peptidomimetic compounds and methods related thereto. The compounds of the present invention may be synthesized using these methods.

In addition to the agents disclosed herein having naturally-occurring amino acids with peptide or unnatural linkages, the present invention also provides for other structurally similar compounds or agents such as polypeptide analogs with unnatural amino acids in the compound. Such compounds may be readily synthesized on a peptide synthesizer available from vendors such as Applied Biosystems, Dupont and Millipore.

The present invention provides for a method for treating a subject suffering from a neurodegenerative condition which comprises administering to the subject a compound capable of inhibiting binding of ERAB polypeptide to amyloid-beta peptide in the subject and thereby treating the subject suffering from a neurodegenerative condition. This present invention encompasses gene therapy, especially for patients with acute neurodegenerative conditions.

There are several protocols for human gene therapy which have been approved for use by the Recombinant DNA Advisory Committee (RAC) which conform to a general protocol of target cell infection and administration of transfected cells (66, 69, 70). In addition, U.S. Pat. No. 5,399,346 (Anderson, W. F. et al., issued Mar. 21, 1995) describes procedures for retroviral gene transfer (68). The contents of these support references are incorporated in their entirety into the subject application. Retroviral-mediated gene transfer requires target cells which are undergoing cell division in order to achieve stable integration hence, cells are collected from a subject often by removing blood or bone marrow. It may also be possible to remove cerebrospinal fluid or brain tissue. It may be necessary to select for a particular subpopulation of the originally harvested cells for use in the infection protocol. For example, white blood cells may be separated from red blood cells using an apheresis procedure. The white cells may then be placed in culture with mitogens, such as IL-2 or OKT3 (which can stimulate T-cell proliferation) for approximately 18 hrs. Then, a retroviral vector containing the gene(s) of interest would be mixed into the culture medium. The vector binds to the surface of the subject's cells, enters the cells and inserts the gene of interest randomly into a chromosome. The gene of interest is now stably integrated and will remain in place and be passed to all of the daughter cells as the cells grow in number. The cells may be expanded in culture for a total of 9–10 days before reinfusion (69, 70). As the length of time the target cells are left in culture increases, the possibility of contamination also increases, therefore a shorter protocol would be more beneficial.

One skilled in the art would recognize that retroviruses, adenoviruses, parvoviruses, and herpes viruses have been used to transfer genes (77).

The present invention also includes a compound which is capable of inhibiting the enzymatic activity of ERAB polypeptide. The compound may inhibit or alter the synergistic effect of amyloid-beta peptide on ERAB polypeptide. The compound may prevent the interaction of ERAB polypeptide with amyloid-beta peptide thereby altering the enzymatic activity of ERAB polypeptide and thus improving a neurodegenerative condition.

Another embodiment of the present invention is a method for alleviating symptoms of a neurodegenerative condition in a subject which includes administering to the subject a compound described hereinabove, the compound being present in an amount effective to inhibit neuronal cell death and thus alleviate the symptoms of the neurodegenerative condition in the subject.

The neurodegenerative condition may be associated with aging, Alzheimer's disease, dentatorubral and pallidolyusian atrophy, Huntington's disease, Machoado-Joseph disease, multiple sclerosis, muscular dystrophy, Parkinson's disease, senility, spinocerebellar ataxia type I, spinobulbar muscular atrophy, stroke, trauma. The subject may be a mammal. The mammal may be a human. The administration may include aerosol delivery; intralesional, intraperitoneal, intramuscular or intravenous injection; infusion; liposome-mediated delivery; anal, nasal, oral, ocular, otic or topical delivery of the pharmaceutical composition.

In one embodiment, the condition may be associated with degeneration of a neuronal cell in the subject, with formation of an amyloid-beta peptide fibril, with aggregation of amyloid-beta peptide, with infiltration of a microglial cell into a senile plaque, or with activation of a microglial cell by an amyloid-beta peptide, wherein the activation comprises production of cytokines by the microglial cell.

This invention is illustrated in the Experimental Details section which follows. These sections are set forth to aid in an understanding of the invention but are not intended to, and should not be construed to, limit in any way the invention as set forth in the claims which follow thereafter.

EXPERIMENTAL DETAILS

Example 1

ERAB Polypeptide—A Novel Intracellular Amyloid-Beta Peptide Binding Polypeptide which Mediates Neurotoxicity in Alzheimer's Disease Amyloid-beta peptide is neurotoxic and is implicated in the pathogenesis of Alzheimer's disease (1–6). Using the yeast two-hybrid system, a novel endoplasmic reticulum-associated amyloid-beta binding polypeptide (ERAB polypeptide), putatively identified as a hydroxysteroid dehydrogenase, was shown to be expressed in normal tissues and, at higher levels, in affected neurons in the brain in Alzheimer's disease. ERAB polypeptide, constitutively produced by neuroblastoma cells was co-immunoprecipitated with amyloid-beta peptide; following exposure of cultures to exogenous amyloid-beta peptide, ERAB polypeptide was rapidly redistributed to the inner aspect of the plasma membrane. Toxicity of amyloid-beta peptide to neuroblastoma cells was prevented by liposome-mediated introduction of anti-ERAB polypeptide $F(ab')_2$ antibody into the cell and was enhanced by overexpression of ERAB polypeptide in COS cells. These data implicate a novel intracellular binding protein, ERAB polypeptide, as an integral participant in amyloid-beta-cellular interactions, and suggest a mechanism whereby amyloid-beta peptide could gain access to cellular compartments containing ERAB polypeptide. There may be other cell surface molecules capable of tethering amyloid-beta peptide, as indicated by the incomplete blockade of amyloid-beta peptide-cell surface interaction by preventing access to RAGE, and the characterization of other molecules which also bind amyloid-beta peptide, such as the type I macrophage scavenger receptor present on microglia (20–21).

Another potentially important mechanism of cytotoxicity of amyloid-beta peptide species could result from their engagement by intracellular targets. Intracellular accumulation of amyloidogenic amyloid-beta peptide has been observed in several cell types (22–27); this could reflect aberrant cellular processing with excessive amounts of amyloid-beta peptide (≈4 kDa) generated within the cell, or from uptake of amyloid-beta peptide released into the medium. In addition, larger C-terminal fragments of APP might in themselves exert neurotoxic effects. These data led to consideration of the possibility that amyloid-beta peptide and amyloid-beta peptide-containing polypeptides might act at specific intracellular sites relevant to the neurotoxicity underlying AD. Using the yeast two-hybrid system (28–29), an intracellular amyloid-beta peptide binding protein in the endoplasmic reticulum which mediates, at least in part, the ability of amyloid-beta peptide to induce cellular toxicity was identified. These data provide the first direct evidence for an intracellular binding site for amyloid-beta peptide, and indicate that intracellular amyloid-beta peptide, in addition to amyloid-beta peptide in the extracellular space, can exert deleterious effects on cellular functions.

Identification and Cloning of ERAB.

Figure 1A:
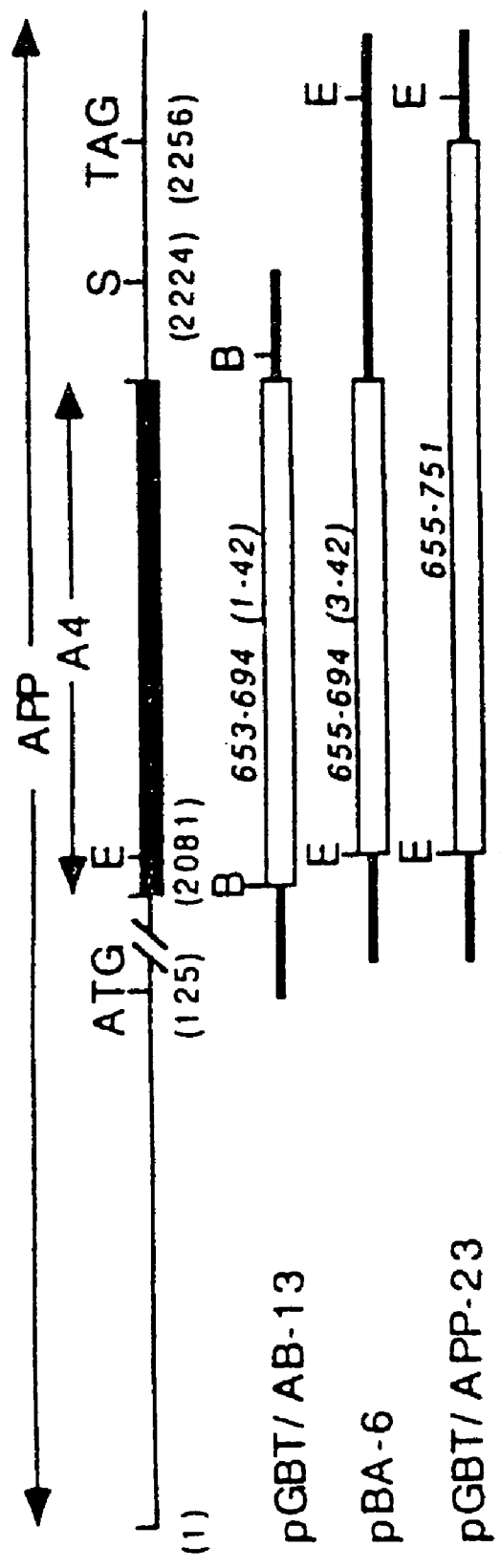
Figure 1B:
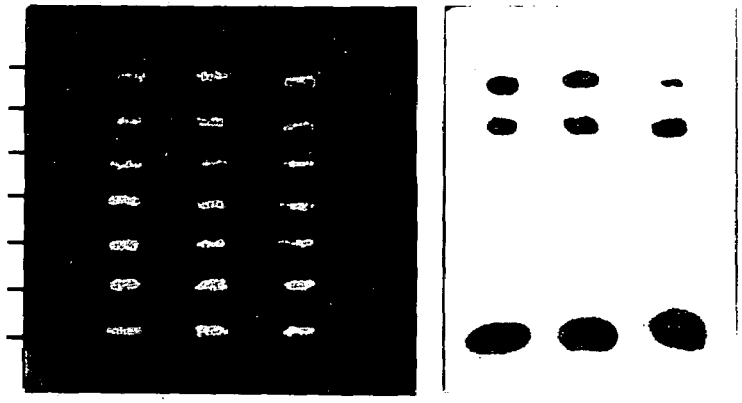
Figure 1C:
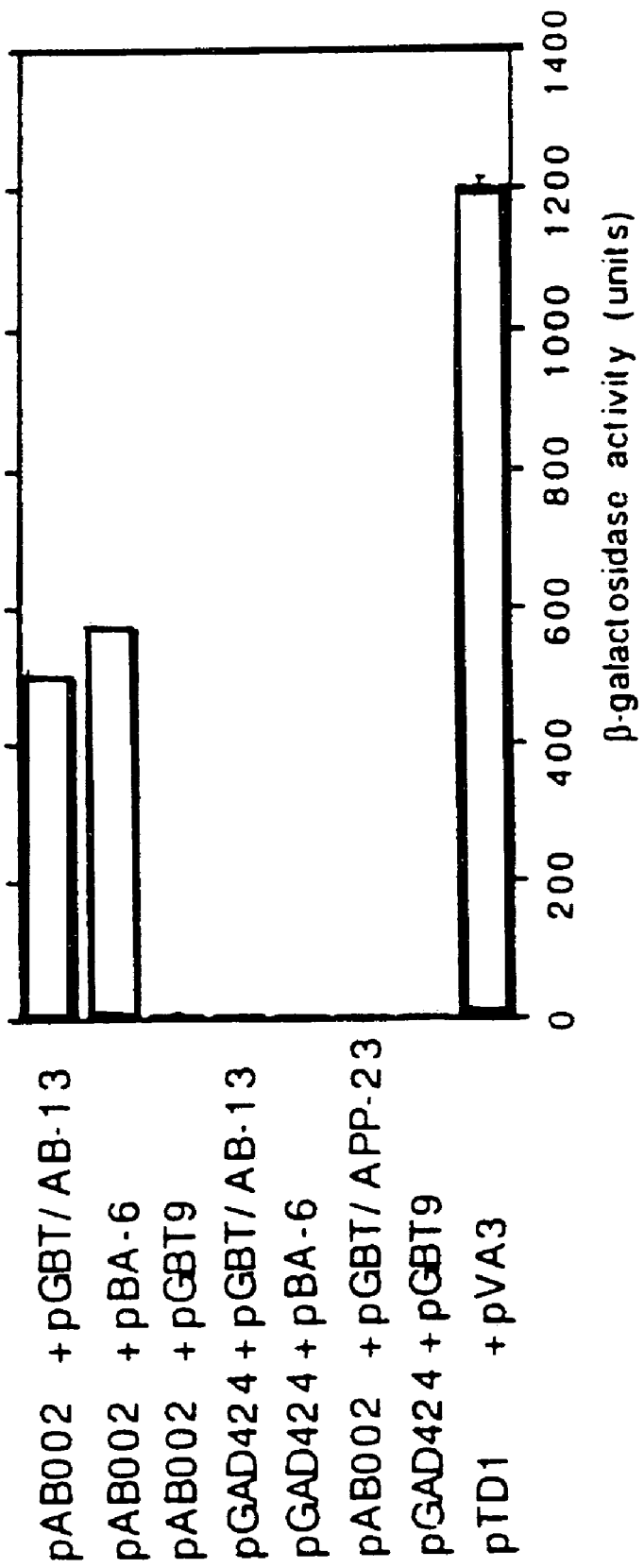

The yeast two-hybrid system was used to screen human brain and HeLa cell Matchmaker T cDNA libraries for encoded proteins capable of binding to the fusion protein containing amyloid-S-peptide. In order to screen the libraries, the portion of human amyloid precursor protein sequence encoding amyloid-beta peptide was subcloned into the yeast expression vector pGBT9 containing the GAL4 DNA-binding domain (FIG. 1A). Out of $3 \times 10^6$ clones screened from each library, one positive clone was identified from human brain and three positive clones from HeLa cells. By DNA sequencing, all four clones (designated as ERAB, see below) gave the same cDNA sequence, except for minor variations at the 5'-end cloning site. Strong β-galactosidase activity was observed when constructs containing nucleic acid encoding amyloid-beta beta peptide (1–42 and 3–42' and ERAB polypeptide were co-expressed (FIGS. 1B and 1C). The specificity of ERAB polypeptide interaction with amyloid-beta peptide in this system was further demonstrated by lack of β-galactosidase activity when the amyloid-beta peptide-related construct or the ERAB nucleic acid construct was replaced with vector-only constructs (FIGS. 1B and 1C). The construct pGBT/APP-23, which contained β-amyloid precursor protein (APP)-derived amino acids 655–751 (encoding a peptide starting at residue 3 in amyloid-beta peptide and extending for 95 amino acids towards the C-terminus), showed no β-galactosidase activity, indicating that the C-terminus of APP prevents amyloid-beta peptide interaction with ERAB polypeptide, suggesting that normally expressed APP is not a ligand for ERAB polypeptide. Using the 5'-rapid amplification of cDNA ends (RACE), the 5'-end of a human ERAB nucleic acid was cloned; the sequence was found to extend about 18 bp upstream of the first AUG and the start codon of the open reading frame was consistent with Kozak consensus sequences (30). The full-length cDNA sequence coded for a predicted 262 amino acid polypeptide (FIG. 1D, Seq. Id. Nos. 1 and 2). Comparison with the SWISS-PROT and Protein Data Bank databases, using the FASTA algorithm (31–32), showed amino acid sequences of ERAB polypeptide to most closely resemble the family of short-chain alcohol dehydrogenases, including hydroxysteroid dehydrogenases, Ke6, and acetoacetyl-CoA reductases (33–34). In both cases, ERAB polypeptide exhibited an identity score of 32% and a similarity score of 65%. Alignment of ERAB polypeptide with the 255 amino acids of the nicotinamide adenine dinucleotide (NAD) binding enzyme 3a, 20β-hydroxysteroid dehydrogenase (EC1.1.1.53) of Streptomyces hydrogenans, for which the X-ray structure at 2.6 Å resolution is available (34), revealed a series of common structural motifs (FIGS. 1E-1 and 1E-2, ERAB as Seq. Id. No. 3 and 2 BHD as Seq. Id. No. 4); both share the NAD (H) binding domains, as well as the highly conserved sequence YGASK in the bacterial enzyme (residues 152–165), which in the human ERAB polypeptide corresponds to residues 168–172 (YSASK), putatively assigned as part of the active center of the enzyme.

To study the ability of ERAB polypeptide to bind amyloid-beta peptide, TrcHis-ERAB fusion protein was expressed in *E. coli* and purified. Immunoblotting with polyclonal antibodies prepared by immunizing an animal with ERAB polypeptide-derived peptides, to produce an anti-ERAB IgG antibody, indicated the presence of the target ERAB polypeptide sequence in the fusion protein, but not in the control fusion protein, TrcHis-chloramphenicol acetyltransferase (CAT) (FIG. 2A; lanes 1–2). The specificity of anti-ERAB polypeptide IgG antibody was shown by its recognition of the TrcHis-ERAB fusion protein when the latter was present in crude cell lysates, and disappearance of this band on addition of excess free ERAB polypeptide-derived peptide identical to that used as immunogen (FIG. 2A, lane 3). Purified TrcHis-ERAB adsorbed to microtiter wells bound $^{125}$I-amyloid-beta peptide (synthetic 1–40) dependent on the amount of immobilized ERAB polypeptide (FIG. 2B), and this was blocked by antibody to ERAB polypeptide but not by nonimmune IgG (FIG. 2C). No specific binding of $^{125}$I-amyloid-beta peptide was observed to wells coated with albumin (FIG. 2B, bar designated "0") or TrcHis-CAT. At one concentration of immobilized TrcHis-ERAB polypeptide, binding of $^{125}$I-amyloid-beta peptide was saturable with $K_d$=51.6±15.7 nM (FIG. 2D). The specificity of freshly prepared $^{125}$I-amyloid-beta peptide (1–40) binding to TrcHis-ERAB polypeptide was shown by competition experiments in which excess unlabelled freshly prepared synthetic amyloid-beta peptide (1–40), synthetic amyloid-beta peptide (1–40) incubated for 3 days at 37° C. (under conditions promoting aggregation) (6), synthetic amyloid-beta peptide (1–20), and AD-derived amyloid-beta peptide (mainly 1–42) blocked binding, but synthetic amyloid-beta peptide (25–35), scrambled amyloid-beta peptide (25–35), and Arg-Gly-Asp-Ser (Seq. ID. No. 5) had no effect (FIG. 2E). Experiments in which TrcHis-ERAB polypeptide was radioiodinated and amyloid-beta peptide (1–42) was adsorbed to microtiter wells also showed similar specific binding dependent on the concentration of amyloid-beta peptide (FIG. 2F). Complementary studies in which a single concentration of amyloid-beta peptide (1–42) was immobilized on wells and varying amounts of $^{125}$I-TrcHis-ERAB were added showed dose-dependent binding with $K_d$=88.3±28.1 nM (FIG. 2G). In contrast, excess unlabelled TrcHis-CAT did not inhibit the binding of $^{125}$I-TrcHis-ERAB to microtiter wells with adsorbed amyloid-beta peptide. These data demonstrate that ERAB polypeptide and amyloid-beta peptide interact specifically in the nanomolar range.

Tissue and Cellular Localization of ERAB

ERAB mRNA was expressed ubiquitously in normal human tissues and brain subregions as a single transcript of ≈1 kb in each case (FIGS. 3A, 3B, and 3C); the highest levels of ERAB transcripts were in liver and heart, but ERAB nucleic acid was also expressed elsewhere, including normal brain. ERAB antigen, detected with anti-ERAB derived polyclonal antibody, was visualized on SDS-PAGE as a ≈29 kDa band in extracts of normal brain from two individuals (FIG. 3D, lanes 3–4). This apparent molecular weight is close to that predicted from analysis of the ERAB polypeptide sequence (26925.7 Daltons). Intensity of the band observed on immunoblots with AD brain from two different patients (FIG. 3D, lanes 1–2) was greater than that observed in brain extracts from age-matched controls (FIG. 3D, lanes 3–4; a total of five AD and three controls were analyzed). The immunoreactive band in AD brain was blocked by addition of excess free TrcHis-ERAB (FIG. 3D, lanes 5–6), but not by free TrcHis-CAT. Immunostaining of normal brain showed ERAB polypeptide to be predominately localized in neurons (FIG. 3E); controls with nonimmune IgG or with anti-ERAB IgG in the presence of excess ERAB peptide were unstained. Increased neuronal ERAB polypeptide expression was observed in AD brain (FIGS. 3F-1), especially near deposits of amyloid-beta peptide (FIGS. 3F-2). These histologic results are representative of seven AD brains and five age-matched normal brains, the postmortem times of which were <8 hrs.

Histologic evidence and the apparent absence of a signal peptide or transmembrane spanning domain indicated that ERAB polypeptide was intracellular. Immunoblotting demonstrated expression of ERAB polypeptide as a single ≈29 kDa band in both human neuroblastoma (SK-N-SH; FIG. 4A, lane 1) and HeLa cells (FIG. 4A, lane 2) whose appearance was blocked by excess free TrcHis-ERAB. Confocal microscopy of HeLa cultures showed ERAB polypeptide to be distributed (FIG. 4B) identically with the endoplasmic reticulum marker protein disulfide isomerase (35) (FIG. 4C), as shown in double immunofluorescence images for both antigens (FIG. 4D). Similar results were obtained with neuroblastoma cells and ERAB-transfected COS cells. In neuroblastoma cells transfected to overexpress ERAB polypeptide, subcellular fractionation showed ERAB antigen in fractions containing the endoplasmic reticulum marker GRP78 (FIG. 4E, lanes 4–5), but not in fractions containing plasma membrane, cytosol, or Golgi (FIG. 4E, lanes 1–3). Based on immunostaining with ERAB IgG and on binding studies with labelled anti-ERAB IgG, ERAB polypeptide was not identified on the cell surface. Furthermore, in studies using markers for mitochondria, lysosomes and Golgi complex, ERAB polypeptide was not found in these compartments. These data suggested that ERAB polypeptide was only present in the endoplasmic reticulum.

These observations also posed an apparent paradox, for, how could amyloid-beta peptide, most of which is extracellular, interact with a polypeptide associated with endoplasmic reticulum? First, it was observed that the presence of amyloid-beta peptide influenced the distribution of ERAB polypeptide; addition of amyloid-beta peptide (1–42) to neuroblastoma cells resulted in a marked change in the cellular localization of ERAS polypeptide from its original intracellular sites (FIG. 4F) to granular-particulate accumulations of apparently associated with the inner aspect of the cell membrane (FIG. 4G; no ERAB polypeptide was detected in nonpermeabilized cells). These changes were specific for amyloid-beta peptide, as neither scrambled amyloid-beta peptide nor an unrelated peptide (Arg-Gly-Asp-Ser) (Seq. ID. No. 5) similarly perturbed the distribution of ERAB polypeptide. Second, it was determined that ERAB polypeptide became associated with amyloid-beta peptide, and that amyloid-beta peptide-induced effects on ERAB polypeptide were not likely mediated by an indirect mechanism. To demonstrate this, SK-N-SH cells were incubated with $^{125}$I-amyloid-beta peptide (1–40), and immunoprecipitation of cell-associated peptide was performed using antibodies to ERAB. From cell lysates, anti-ERAB IgG precipitated $^{125}$I-labelled ≈4 kDa molecule visualized on tris-tricine gels which corresponded to amyloid-beta peptide (FIG. 4H, lane 2), whereas nonimmune IgG did not precipitate any bands (FIG. 4H, lane 1). To confirm that ERAB polypeptide and amyloid-beta peptide interacted in intact cultured cells, neuroblastoma cells were incubated for 6 hrs at 37° C. with $^{125}$I-amyloid-beta peptide followed by addition of the crosslinker disuccinimidyl suberate (FIG. 4I). Cultures were then washed extensively, to remove unbound tracer and unreacted crosslinker, followed by lysis of the cells and immunoprecipitation with anti-ERAB IgG or nonimmune IgG. Antibody to ERAB polypeptide precipitated a $^{125}$I-labelled band with Mr ≈38 kDa (FIG. 4I, lane 2), most likely corresponding to a complex of ERAB polypeptide with an oligomer (dimer-trimer) of $^{125}$I-amyloid-beta peptide; in contrast, no bands were precipitated with nonimmune IgG (FIG. 4I, lane 1). These data show that amyloid-beta peptide directly affects the cellular distribution of ERAB polypeptide, and that ERAB polypeptide-amyloid-beta peptide interaction occurs in intact cells.

ERAB Polypeptide Contributes to Amyloid-Beta Peptide-Mediated Cellular Toxicity.

Elucidating the role of ERAB polypeptide in amyloid-beta peptide-induced cellular stress was critical to evaluating its functional significance. Following transfection, COS-1 cells overexpressed ERAB polypeptide (FIG. 5A, lane 2), compared with mock-transfected cultures (FIG. 5A, lane 1). Exposure to amyloid-beta peptide of cultures overexpressing ERAB polypeptide suppressed their capacity to reduce 3-(4,5-dimethylthiazol-2-yl)-2,5, diphenyl tetrazolium bromide (MTT) (36), as compared with mock-transfected controls (FIG. 5B). COS cells were then transfected with vectors causing overexpression of either ERAB polypeptide, amyloid-beta peptide or both ERAB polypeptide and amyloid-beta peptide. In cells transfected with the plasmid causing overexpression of amyloid-beta peptide there were increased levels of amyloid-beta peptide, both cell-associated peptide and that released into the medium, which reached a maximum after 24 hrs. Cells transfected with pcDNA3-ERAB nucleic acid showed increased expression of ERAB polypeptide which was only cell-associated. Cytotoxicity was especially evident in COS cells cotransfected with vectors causing overexpression of both ERAB polypeptide and amyloid-beta peptide: compared with COS-1 transfected with vector alone (FIG. 5C), or those overexpressing only ERAB polypeptide (FIG. 5D) or amyloid-beta peptide (FIG. 5E), cells from cultures cotransfected with both ERAB nucleic acid and amyloid-beta peptide appeared shrunken and clumped (FIG. 5F).

The effect of ERAB nucleic acid and protein expression on sensitivity of neuroblastoma cells (which normally express ERAB polypeptide) to amyloid-beta peptide-induced stress was studied using blocking F(ab')$_2$ prepared from anti-ERAB IgG. For these studies, anti-ERAB or nonimmune F(ab')$_2$ was introduced into neuroblastoma cells using lipofectamine. In each case, the F(ab')$_2$ fragments became cell-associated (FIGS. 6A–B). After liposome-mediated introduction of the F(ab')$_2$, SK-N-SH cultures were incubated with a range of amyloid-beta peptide concentrations; whereas cultures exposed to nonimmune-derived F(ab')$_2$ showed marked amyloid-beta peptide-induced suppression of MTT reduction (comparable to untreated controls, anti-ERAB-derived F(ab')$_2$ protected against amyloid-beta peptide-induced suppression of MTT reduction (FIG. 6C). In contrast, addition of anti-ERAB F(ab')$_2$ directly to the medium (i.e., not in liposomes) had no affect on amyloid-beta peptide-induced MTT suppression, consistent with the intracellular localization of ERAB polypeptide. Paralleling the protective effect of blocking ERAB polypeptide intracellularly, introduction of anti-ERAB F(ab')$_2$ into SK-N-SH cells using liposomes suppressed amyloid-beta peptide-induced changes in cellular morphology. Control SK-N-SH cultures display typical short neurites and an extended cell body (FIG. 6D); but, after exposure to amyloid-beta peptide, retraction of neurites and rounding up of cell bodies was observed (FIG. 6E). Introduction of anti-ERAB F(ab')$_2$ into SK-N-SH cells prevented, in large part, these amyloid-beta peptide-induced morphologic changes (FIG. 6F), whereas F(ab')$_2$ derived from nonimmune IgG had no effect (FIG. 6G).

Discussion

Neurotoxicity in Alzheimer's disease may result from a concatenation of factors, such as: (1) enhanced cellular processing of APP, releasing amyloidogenic amyloid-beta peptide peptides; (2) interaction of amyloid-beta peptide with cell membranes, both at specific cell binding sites and, presumably, by direct actions on the membrane itself; (3) nonenzymatic glycation of macromolecules whose turnover is delayed in AD brain, producing modified structures which can form crosslinks and generate reactive oxygen intermediates; and, (4) cellular components that comprise the protective response to oxidant stress and/or increase susceptibility to apoptotic stimuli (1–6, 15,16,36–40). Mutant presenilins, associated with most familiar forms of Alzheimer's disease (11–12) and present in endoplasmic reticulum and Golgi complex (41), provide an instructive example of this multifactorial pathogenesis. Increased production of amyloid-beta peptide occurs in transgenic mice overexpressing mutant presenilins, and in the plasma and cultured fibroblasts from carriers of familial AD linked to chromosome 1 (42–44). In addition, presenilin 2, which is homologous to ALG-3, a protein involved in programmed cell death, can function as a susceptibility factor for apoptosis in differentiated PC12 cells, in response to growth factor/serum withdrawal or to addition of amyloid-beta peptide (45).

ERAB polypeptide adds a new dimension to the pathogenetic interaction of amyloid-beta peptide with cellular elements. Like presenilin 2 (45), ERAB polypeptide also appears to potentiate cellular perturbations due to amyloid-beta peptide. However, the true physiologic roles of both ERAB polypeptide and presenilins remain unknown. Addition of amyloid-beta peptide to COS cells overexpressing ERAB polypeptide caused more exaggerated suppression of MTT reduction, and greater retraction of the cells than that induced by the peptide alone. Similarly, in neuroblastoma cells, which constitutively express ERAB polypeptide, amyloid-beta peptide-induced impairment of MTT reduction and of cell morphology were suppressed by introduction of anti-ERAB F(ab')$_2$. Therefor it was proposed that ERAB polypeptide may contribute to AD pathology as a progression factor, enhancing cellular stress due to increased levels of amyloid-beta peptide. Although the mechanism through which ERAB polypeptide promotes amyloid-beta peptide-mediated changes in cellular functions is not clear, ERAB polypeptide and amyloid-beta peptide appear to interact in intact cells. First, addition of amyloid-beta peptide to cells expressing ERAB polypeptide changes its intracellular distribution. Second, COS cells, transfected to overexpress ERAB polypeptide and then exposed to exogenous $^{125}$I-amyloid-beta peptide, formed immunoprecipitable ERAB-$^{125}$I-amyloid-beta peptide complexes. Radioligand binding studies indicated the specificity of ERAB-amyloid-beta peptide interaction, but it is not yet known whether ERAB polypeptide binds preferentially to monomer, oligomer, or fibrillar forms of amyloid-beta peptide. A cross-linking study with $^{125}$I-amyloid-beta peptide-ERAB polypeptide strongly suggests that a soluble, probably dimer or small oligomer of amyloid-beta peptide (46–47) can serve as a ligand for ERAB polypeptide.

Analysis of the ERAB nucleic acid and protein sequence has suggested that ERAB polypeptide might be a part of the cellular enzymatic machinery, possibly functioning as a hydroxysteroid dehydrogenase. The interaction of amyloid-beta peptide with such an intracellular polypeptide is certainly not something that would have been predicted. However, there may be an analogy in binding of glyceraldehyde-3-phosphate dehydrogenase to the expanded polyglutamine repeats coded for by the CAG triplet (48) in mutant forms of the Huntington protein (49), and in other polypeptides associated with other neurodegenerative conditions (49–52). There may be an effect of amyloid-beta peptide on the enzymatic activity of ERAB polypeptide. But, how can amyloid-beta peptide gain access to this intracellular polypeptide which is apparently confined to the endoplasmic reticulum? After addition of amyloid-beta peptide to neuroblastoma cultures expressing ERAB polypeptide, it still cannot be detected on the cell surface. Thus, in order for ERAS polypeptide to interact with amyloid-beta peptide, the amyloidogenic peptide must gain access to the proper intracellular compartment. In this context, although some past studies have demonstrated amyloid-beta peptide aggregates and amyloid fibrils within cells (53–59). Such deposits, however, are usually localized to an endosomal-lysosomal compartment. The association of amyloid-beta peptide with intracellular neurofibrillary tangles has also been noted, suggesting that some amyloid-beta peptide gains access to the cytosolic milieu (it would be difficult to visualize the free ERAS peptide unless becomes associated to a morphologically identifiable structure, such as a neurofibrillary tangle or an amyloid fibril). Potentially, following endocytosis, amyloid-beta peptide could be diverted from the endosomal-lysosomal compartment, where it is also generated (1–6), at least in part, and gain access to the endoplasmic reticulum by a pathway yet to be defined. Alternatively, based on the location of cleavage sites in APP which produce amyloid-beta peptide, including one within the transmembrane spanning domain (1–6), another possible mechanism might be release of peptide to both intra- and extra-cellular spaces.

ERAB transcripts are apparently widely distributed in the body, with highest expression in normal liver and heart. It is possible that ERAB polypeptide participates in homeostatic cellular functions. By virtue of its localization in the endoplasmic reticulum, it may usually function in cellular metabolism, perhaps as a dehydrogenase in steroid biogenesis. ERAB polypeptide may modulate cellular function in normal and perturbed cells.

Example 2

ERAB is Critical for ERAB Potentiation of Amyloid-Beta Cytotoxicity

The following data indicates that an inhibitor of ERAB activity could provide a therapy to protect neurons from Alzheimer's disease.

A mutant of ERAB was created in which tyrosine (169) and lysine (173) were replaced by glycine. These two residues, tyrosine and lysine, are essential components of the active site of ERAB which is an enzyme. The mutant ERAB was expressed and characterized as follows: (1) its immunoblotting showed the same molecular weight (about 27,000 Da) as the native ERAB which is expected for the small change introduced by the mutation, (2) the mutant form is devoid of enzyme activity because enzyme assays for ERAB activity as an NAD-dependent short chain alcohol dehydrogenase (octanol as the substrate) showed no activity and the mutant ERAB did showed no activity towards 17-beta-estradiol (whereas native ERAB is an hydroxysteroid dehydrogenase) or towards S-acetoacetyl-Coenzyme A (whereas native ERAB is an hydroxyacyl Coenzyme A dehydrogenase), (3) when cells were transfected with the mutant ERAB with mutant amyloid-beta precursor protein which produces more amyloid-beta peptide, no increased toxicity to the cell was observed which contrasts with the increased apoptosis, as measured by ELISA for cytoplasmic histone-associated DNA fragments, caused by the cotransfection of wild-type ERAB with mutant amyloid-beta precursor protein.

These findings indicate that an inhibitor of ERAB could protect neurons from the toxic effects of amyloid-beta peptide.

FIG. 7 shows that expression of a mutant form of beta-amyloid precursor protein (βAPP), which causes increased expression of amyloid-beta protein (Aβ) and ERAB causes increased toxicity (DNA fragmentation) to COS cells.

Experimental Procedure:

COS cells were grown in cell culture and transfected using lipofectamine procedure with the following DNA constructs:

1. Wild-type ERAB.

2. Mutant ERAB. This was made by site-directed mutagenesis resulting in replacement of tyrosine [169] and lysine [173]with glycine (at 169 and 173). Mutant ERAB results in the expression of a protein of molecular weight ≈27 kDa which has no enzymatic activity compared with native wild-type ERAB. Native or wild-type ERAB has three distinct enzymatic activities which were assayed: (a) short chain alcohol dehydrogenase (octanol as the substrate); (b) β-hydroxyacyl-Coenzyme A dehydrogenase (S-acetoacetyl-Coenzyme A as substrate); and (c) hydroxysteroid dehydrogenase (17-β-estradiol as the substrate).

3. Mutant βAPP. This was derived from the London mutation of βAPP in which valine at position 717 is replaced by glycine. A reference describing a plasmid which can be used to express this molecule is Wild-Bode, C et al. (1997) Intracellular generation and accumulation of amyloid β-peptide termination at amino acid 42. J. Biol. Chem. 272: 16085–16088.

The assay for cell toxicity was measurement of DNA fragmentation by determining cytoplasmic histone-associated DNA fragments (one could use Cell Death ELISA from Boehringer-Mannheim®).

Experimental Protocol:

Cells were transfected with either wild type ERAB alone, mutant βAPP alone, mutant ERAB alone or lipofectamine alone. Lipofectamine is the lipid to make the vesicles for transfection and serves as a negative control. Cells were cotransfected with either wild type ERAB and mutant βAPP (see FIG. 7; wt-ERAB/mut-APP) or mutant ERAB and mutant APP (see FIG. 7; mut-ERAB/mut-APP).

Cells were allowed to incubate for 24 hours at 37° C., and then the cell death ELISA assay was performed.

RESULTS

Increased DNA fragmentation, consistent with the occurrence of apoptosis (programmed cell death) occurred in cells cotransfected with wild type ERAB and mutant βAPP. This did not occur when cells were transfected with either wild type ERAB or mutant βAPP alone. In contrast, cells cotransfected with mutant ERAB and mutant βAPP did NOT show increased DNA fragmentation. Expression of mutant ERAB and mutant βAPP was confirmed by Western blotting, thus the proteins are expressed but apoptosis did not occur.

Thus, the enzymatically inactivated ERAB does not promote the toxicity of Aβ in the same manner as wild type Aβ. Note that mutant βAPP produces increased amounts of Aβ and causes cytotoxicity which is enhanced by ERAB.

REFERENCES

1. Haass, C & Selkoe, D. *Cell* 7:1039–1042 (1994).
2. Kosik, K. *J. Cell Biol.* 127:1501–1504 (1994).
3. Yankner, B. et al. *Science* 245:417–420 (1989).
4. Scheuner, D. et al. *Nature Med.* 2:864–869 (1996).
5. Roses, A. *Nature Med.* 2:267–269 (1996).
6. Cai, X. et al. *Science* 259:514–516 (1993).
7. Citron, M. et al. *Nature* 360:672–674 (1992).
8. Hendriks, L. et al. *Nature Genet.* 1:218–222 (1992).
9. Mullan, M. et al. *Nature Genet.* 1:345–347 (1992).
10. Haass, C. et al. *J. Biol. Chem.* 269:17741–17748 (1994).
11. Sherrington, R. et al. *Nature* 375:754–760 (1993).
12. Citron, M. et al. *Nature Med.* 3:67–72 (1997).
13. Levy-Lahad, E. et al. *Science* 269:970–972 (1995).
14. Hensley, K. et al. *Proc. Natl. Acad. Sci. (USA)* 91:3270–3274 (1994).
15. Mattson, M. and Goodman, Y. *Brain Res.* 676:219–224 (1995).
16. Mattson, M. *Neurobiol. Aging* 16:661–674 (1995).
17. Yankner, B. et al. *Science* 250:279–282 (1990).
18. Boland, K. et al. *J. Biol. Chem.* 271:18032–18044 (1996).
19. Yan, S-D. et al. *Nature* 382:685–691 (1996).
20. Paresce, D. et al. *Neuron* 17:553–565(1996).
21. El-Khoury, J. et al. *Nature* 382:716–719 (1996).
22. Yoshikawa, K. et al. *Nature* 359:64–67 (1992).
23. Fukuchi, K. et al. *Biochem. Biophys. Res. Commun.* 182:165–173 (1992).
24. Martin, B. et al. *J. Biol. Chem.* 270:26727–26730 (1995).
25. Fuller, S. et al. *Biochemistry* 34:8091–8098 (1995).
26. Matsumoto, A. *Biochim. Biophys. Acta* 1225:304–310 (1994).
27. Frackowiak, J. et al. *Brain. Res.* 676:225–230 (1995).
28. Fields, S. and Song, O-K. *Nature* 340:245–246 (1991).
29. Chien, C-T. et al. *PNAS(USA)* 88:9578–9582 (1991)
30. Kozak, M. *Nucleic Acids Res.* 15:8125–8131 (1987).
31. Bernstein, F. et al. *J. Mol. Biol.* 112:535–542 (1977).
32. Devereux, J. et al. *Nucleic Acids. Res.* 12:387–395 (1984).
33. Ghosh, D. et al. *PNAS(USA)* 88:10064–10068 (1991).
34. Schembri, M. et al. *J. Bacteriol.* 177:4501–4507 (1995).
35. Edman, J. et al. *Nature* 317:267–270 (1985).
36. Behl, C. et al. *Cell* 77:817–827 (1994).
37. Busciglio, J. and Yankner, B. *Nature* 378:776–779 (1995).
38. Vitek, M. et al. *PNAS(USA)* 91:4766–4770 (1994).
39. Yan, S-D. et al. *PNAS(USA)* 91:7787–7791 (1994).
40. Ledesma, M. et al. *J. Biol. Chem.* 269:21614–2169 (1994).
41. Kovacs, D. et al. *Nature Med.* 2:224–229 (1996).
42. Duff, K. et al. *Nature* 383:710–713 (1996).
43. Borchelt, D. et al. *Neuron* 17:1005–1013 (1996).
44. Scheuner, D. et al. *Nature Med.* 2:864–869 (1996).
45. Wolozin, B. et al. *Science* 274:1710–1713 (1996).
46. Kuo, Y-M. et al. *J. Biol. Chem.* 271:4077–4081 (1996).
47. Roher, A. et al. *J. Biol. Chem.* 271:20631–20635 (1996).
48. Burke, J. R. et al. *Nature Med.* 2:347–350 (1996).
49. Huntington's Disease Collaborative Research Group *Cell* 72:971–983 (1993).
50. Koide, R. et al. *Nature Genet.* 6:9–13 (1994).
51. Nagafushi, S. et al. *Nature Genet.* 6:14–18 (1994).
52. Willems, P. *Nature Genet.* 8:213–215 (1994).
53. Knauer, M. et al. *PNAS(USA)* 89:7437–7441 (1992).
54. Perry, G. et al. *Am. J. Pathol.* 40:283–290 (1992).
55. Scott, R et al. *J. Biol. Chem.* 271:8966–8970 (1996).
56. Fuller, S. et al. *Biochem.* 34:8091–8098 (1995).
57. Perry, G. et al. *Am. J. Pathol.* 143:1586–1593 (1993).
58. Yang, A. et al. *J. Biol. Chem.* 270:14786–14792 (1995).
59. Martin, B. et al. *J. Biol. Chem.* 270:26727–2673C 1995).
60. Klotz, I. and Hunston, D. *J. Biol. Chem.* 258:11442–11445 (1984).
61. Roher, A. et al. *J. Biol. Chem.* 268:3072–3083 (1993).
62. David, G. and Reisfeld, R. *Biochem.* 13:1014–1029 (1974).
63. Kuwabara, K. et al. *J. Biol. Chem.* 271:5025–5032 (1996).
64. Adelman, M. et al. *Cell Biol.* 56:191–205 (1973).
65. Yan, S-D. et al. *Nature Med.* 1:693–699 (1995).
66. Anderson, W. F. (1992) Human Gene Therapy. *Science* 256:808–813.
67. Anderson W. F. et al. (1990) Human Gene Therapy 1(3):327–62.
68. Anderson, W. F. et al. Gene Therapy, U.S. Pat. No. 5,399,346, Mar. 21, 1995, filed Mar. 30, 1994, U.S. Ser. No. 220,175.
69. Culver, K. W. et al. (1991a) Lymphocyte Gene Therapy, Human Gene Therapy 2(2):107–9.
70. Culver K. W. et al. (1991b) Transplantation Proceedings (1 Pt 1):170–1.
71. Larrick J. W. and Burck K. L. (1991) Gene Therapy: Application of Molecular Biology, New York, Elsevier.
72. Miller A. D. (1990) *Blood* 76: (2):271–8.
73. Miller A. D. (1990) Retrovirus Packaging Cells, Human Gene Therapy 1(1):5–14.
74. Miller A. D. (1992) Human Gene Therapy Comes of Age. *Nature* 357:455–460.
75. Miller A. D. and Buttimore C. (1986) Redesign of retrovirus packaging cell lines to avoid recombination leading to helper virus production. *Molec. Cell Biol.* 6:2895–2902.
76. Miller A. D. et al. (1991) Construction and properties of retrovirus packaging cells based on Gibbon Ape Leukemia Virus. *J. Virol.* 65:2220–2224.
77. Mulligan, R. C. (1993). The basic science of gene therapy. *Science* 260:926–932.
78. Rosenberg S. A. et al. (1990) Gene transfer into humans—immunotherapy of patients with advanced melanoma, using tumor-infiltrating lymphocytes modified by retroviral gene transduction. *New England Journal of Medicine* 323:570–8.
79. Sambrook et al. (1989) *Molecular Cloning: A Laboratory Manual*, 2nd Ed.

80. Abuchowski et al., In: "Enzymes as Drugs", Holcenberg et al., eds. Wiley-Interscience, New York, N.Y., 367–383 (1981).
81. Carpenter et al., *Toxicol. Appl. Pharmacol.*, 18:35–40 (1971).
82. Katre et al., *Proc. Natl. Acad. Sci. USA* 84:1487–1491 (1987).
83. Newmark et al., *J. Appl. Biochem.* 4:185–189 (1982).
84. Stryer, L. (1988) *Biochemistry*.
85. Benet, et al., "Clinical Pharmacokinetics" in ch. 1 (pp. 20–32) of Goodman and Gilman's The Pharmacological Basis of Therapeutics, 8th edition, A. G. Gilman, et al. eds. (Pergamon, N.Y. 1990).
86. Dayhoff. (1988) *Atlas of Protein Sequence and Structure*.
87. U.S. Pat. No. 5,219,990.
88. Kriegler, M. (1990) *Gene Transfer and Expression: A Laboratory Manual*, Stockton Press, New York, N.Y.

What is claimed is:

1. A method for determining whether an agent inhibits binding of human ERAB polypeptide (SEQ. ID. NO: 2), or a fragment thereof, to amyloid-beta peptide which comprises:
   (a) incubating human ERAB polypeptide (SEQ. ID. NO: 2), or a fragment thereof, the agent and amyloid-beta peptide under suitable binding conditions;
   (b) determining the amount of amyloid-beta peptide bound to the polypeptide or fragment from the incubate of (a); and
   (c) comparing the amount of bound amyloid-beta peptide determined in step (b) to an amount of amyloid-beta peptide bound to the polypeptide or fragment determined in the absence of the agent, wherein when the amount of amyloid-beta polypeptide bound to the polypeptide or fragment thereof is decreased in the presence of said agent, the agent inhibits binding of human ERAB polypeptide (SEQ. ID. NO: 2), or the fragment thereof.

2. The method of claim 1, wherein the agent is a peptide.

3. The method of claim 1, wherein the agent is a peptidomimetic compound.

4. The method of claim 1, wherein the agent is a nucleic acid.

5. The method of claim 1, wherein the agent is a small molecule.

* * * * *

SEQUENCE LISTING (1) GENERAL INFORMATION:

(iii) NUMBER OF SEQUENCES: 5

(2) INFORMATION FOR SEQ ID NO: 1:

(i) SEQUENCE CHARACTERISTICS:
      (A) LENGTH: 981 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 19..801

(xi) SEQUENCE DESCRIPTION: SEQ ID NO: 1:

```
GGAGTGGCCG GCGACAAG ATG GCA GCA GCG TGT CGG AGC GTG AAG GGC CTG        51
                    Met Ala Ala Ala Cys Arg Ser Val Lys Gly Leu
                     1               5                  10

GTG GCG GTA ATA ACC GGA GGA GCC TCG GGC CTG GGC CTG GCC ACG GCG        99
Val Ala Val Ile Thr Gly Gly Ala Ser Gly Leu Gly Leu Ala Thr Ala
             15                  20                  25

GAG CGA CTT GTG GGG CAG GGA GCC TCT GCT GTG CTT CTG GAC CTG CCC       147
Glu Arg Leu Val Gly Gln Gly Ala Ser Ala Val Leu Leu Asp Leu Pro
         30                  35                  40

AAC TCG GGT GGG GAG GCC CAA GCC AAG AAG TTA GGA AAC AAC TGC GTT       195
Asn Ser Gly Gly Glu Ala Gln Ala Lys Lys Leu Gly Asn Asn Cys Val
     45                  50                  55

TTC GCC CCA GCC GAC GTG ACC TCT GAG AAG GAT GTG CAA ACA GCT CTG       243
Phe Ala Pro Ala Asp Val Thr Ser Glu Lys Asp Val Gln Thr Ala Leu
 60                  65                  70                  75

GCT CTA GCA AAA GGA AAG TTT GGC CGT GTG GAT GTA GCT GTC AAC TGT       291
Ala Leu Ala Lys Gly Lys Phe Gly Arg Val Asp Val Ala Val Asn Cys
                 80                  85                  90

GCA GGC ATC GCG GTG GCT AGC AAG ACG TAC AAC TTA AAG AAG GGC CAG       339
Ala Gly Ile Ala Val Ala Ser Lys Thr Tyr Asn Leu Lys Lys Gly Gln
             95                 100                 105

ACC CAT ACC TTG GAA GAC TTC CAG CGA GTT CTT GAT GTG AAT CTC ATG       387
Thr His Thr Leu Glu Asp Phe Gln Arg Val Leu Asp Val Asn Leu Met
        110                 115                 120

GGC ACC TTC AAT GTG ATC CGC CTG GTG GCT GGT GAG ATG GGC CAG AAT       435
Gly Thr Phe Asn Val Ile Arg Leu Val Ala Gly Glu Met Gly Gln Asn
    125                 130                 135

GAA CCA GAC CAG GGA GGC CAA CGT GGG GTC ATC ATC AAC ACT GCC AGT       483
Glu Pro Asp Gln Gly Gly Gln Arg Gly Val Ile Ile Asn Thr Ala Ser
140                 145                 150                 155

GTG GCT GCC TTC GAG GGT CAG GTT GGA CAA GCT GCA TAC TCT GCT TCC       531
Val Ala Ala Phe Glu Gly Gln Val Gly Gln Ala Ala Tyr Ser Ala Ser
                160                 165                 170
```

```
AAG GGG GGA ATA GTG GGC ATG ACA CTG CCC ATT GCT CGG GAT CTG GCT      579
Lys Gly Gly Ile Val Gly Met Thr Leu Pro Ile Ala Arg Asp Leu Ala
            175                 180                 185

CCC ATA GGT ATC CGG GTG ATG ACC ATT GCC CCA GGT CTG TTT GGC ACC      627
Pro Ile Gly Ile Arg Val Met Thr Ile Ala Pro Gly Leu Phe Gly Thr
            190                 195                 200

CCA CTG CTG ACC AGC CTC CCA GAG AAA GTG TGC AAC TTC TTG GCC AGC      675
Pro Leu Leu Thr Ser Leu Pro Glu Lys Val Cys Asn Phe Leu Ala Ser
            205                 210                 215

CAA GTG CCC TTC CCT AGC CGA CTG GGT GAC CCT GCT GAG TAT GCT CAC      723
Gln Val Pro Phe Pro Ser Arg Leu Gly Asp Pro Ala Glu Tyr Ala His
220             225                 230                 235

CTC GTA CAG GCC ATC ATC GAG AAC CCA TTC CTC AAT GGA GAG GTC ATC      771
Leu Val Gln Ala Ile Ile Glu Asn Pro Phe Leu Asn Gly Glu Val Ile
                240                 245                 250

CGG CTG GAT GGG GCC ATT CGT ATG CAG CCT TGAAGGGAGA AGGCAGAGAA        821
Arg Leu Asp Gly Ala Ile Arg Met Gln Pro
                255                 260

AACACACGCT CCTCTGCCCT TCCTTTCCCT GGGGTACTAC TCTCCAGCTT GGGAGGAAGC    881

CCAGTAGCCA TTTTGTAACT GCCTACCAGT CGCCCTCTGT GCCTAATAAA GTCTCTTTTT    941

CTCACAAAAA AAAAAAAAAA AAAAAAAAAA AAAAAAAAA                          981

(2) INFORMATION FOR SEQ ID NO: 2:

(i) SEQUENCE CHARACTERISTICS:
        (A) LENGTH: 261 amino acids
        (B) TYPE: amino acid
        (D) TOPOLOGY: linear (ii) MOLECULE TYPE: protein (xi) SEQUENCE DESCRIPTION: SEQ ID NO: 2:

Met Ala Ala Cys Arg Ser Val Lys Gly Leu Val Ala Val Ile Thr
1               5                   10                  15

Gly Gly Ala Ser Gly Leu Gly Leu Ala Thr Ala Glu Arg Leu Val Gly
                20                  25                  30

Gln Gly Ala Ser Ala Val Leu Leu Asp Leu Pro Asn Ser Gly Gly Glu
            35                  40                  45

Ala Gln Ala Lys Lys Leu Gly Asn Asn Cys Val Phe Ala Pro Ala Asp
        50                  55                  60

Val Thr Ser Glu Lys Asp Val Gln Thr Ala Leu Ala Leu Ala Lys Gly
65                  70                  75                  80

Lys Phe Gly Arg Val Asp Val Ala Val Asn Cys Ala Gly Ile Ala Val
                85                  90                  95

Ala Ser Lys Thr Tyr Asn Leu Lys Lys Gly Gln Thr His Thr Leu Glu
            100                 105                 110

Asp Phe Gln Arg Val Leu Asp Val Asn Leu Met Gly Thr Phe Asn Val
        115                 120                 125

Ile Arg Leu Val Ala Gly Glu Met Gly Gln Asn Glu Pro Asp Gln Gly
    130                 135                 140

Gly Gln Arg Gly Val Ile Ile Asn Thr Ala Ser Val Ala Ala Phe Glu
145                 150                 155                 160

Gly Gln Val Gly Gln Ala Ala Tyr Ser Ala Ser Lys Gly Gly Ile Val
                165                 170                 175

Gly Met Thr Leu Pro Ile Ala Arg Asp Leu Ala Pro Ile Gly Ile Arg
            180                 185                 190
```

```
Val Met Thr Ile Ala Pro Gly Leu Phe Gly Thr Pro Leu Leu Thr Ser
    195                 200                 205

Leu Pro Glu Lys Val Cys Asn Phe Leu Ala Ser Gln Val Pro Phe Pro
210                 215                 220

Ser Arg Leu Gly Asp Pro Ala Glu Tyr Ala His Leu Val Gln Ala Ile
225                 230                 235                 240

Ile Glu Asn Pro Phe Leu Asn Gly Glu Val Ile Arg Leu Asp Gly Ala
                245                 250                 255

Ile Arg Met Gln Pro
            260

(2) INFORMATION FOR SEQ ID NO: 3:

(i) SEQUENCE CHARACTERISTICS:
        (A) LENGTH: 261 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 3:

Met Ala Ala Ala Cys Arg Ser Val Lys Gly Leu Val Ala Val Ile Thr
1               5                   10                  15

Gly Gly Ala Ser Gly Leu Gly Leu Ala Thr Ala Glu Arg Leu Val Gly
                20                  25                  30

Gln Gly Ala Ser Ala Val Leu Leu Asp Leu Pro Asn Ser Gly Gly Glu
            35                  40                  45

Ala Gln Ala Lys Lys Leu Gly Asn Asn Cys Val Phe Ala Pro Ala Asp
    50                  55                  60

Val Thr Ser Glu Lys Asp Val Gln Thr Ala Leu Ala Leu Ala Lys Gly
65                  70                  75                  80

Lys Phe Gly Arg Val Asp Val Ala Val Asn Cys Ala Gly Ile Ala Val
                85                  90                  95

Ala Ser Lys Thr Tyr Asn Leu Lys Lys Gly Gln Thr His Thr Leu Glu
                100                 105                 110

Asp Phe Gln Arg Val Leu Asp Val Asn Leu Met Gly Thr Phe Asn Val
            115                 120                 125

Ile Arg Leu Val Ala Gly Glu Met Gly Gln Asn Glu Pro Asp Gln Gly
    130                 135                 140

Gly Gln Arg Gly Val Ile Ile Asn Thr Ala Ser Val Ala Ala Phe Glu
145                 150                 155                 160

Gly Gln Val Gly Gln Ala Ala Tyr Ser Ala Ser Lys Gly Gly Ile Val
                165                 170                 175

Gly Met Thr Leu Pro Ile Ala Arg Asp Leu Ala Pro Ile Gly Ile Arg
            180                 185                 190

Val Met Thr Ile Ala Pro Gly Leu Phe Gly Thr Pro Leu Leu Thr Ser
    195                 200                 205

Leu Pro Glu Lys Val Cys Asn Phe Leu Ala Ser Gln Val Pro Phe Pro
210                 215                 220

Ser Arg Leu Gly Asp Pro Ala Glu Tyr Ala His Leu Val Gln Ala Ile
225                 230                 235                 240

Ile Glu Asn Pro Phe Leu Asn Gly Glu Val Ile Arg Leu Asp Gly Ala
                245                 250                 255

Ile Arg Met Gln Pro
            260
```

(2) INFORMATION FOR SEQ ID NO: 4:

(i) SEQUENCE CHARACTERISTICS:
        (A) LENGTH: 255 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 4:

```
Met Asn Asp Leu Ser Gly Lys Thr Val Ile Ile Thr Gly Ala Arg
 1               5                  10                  15

Gly Leu Gly Ala Glu Ala Ala Arg Gln Ala Val Ala Ala Gly Ala Arg
             20                  25                  30

Val Val Leu Ala Asp Val Leu Asp Glu Glu Gly Ala Ala Thr Ala Arg
             35                  40                  45

Glu Leu Gly Asp Ala Ala Arg Tyr Gln His Leu Asp Val Thr Ile Glu
             50                  55                  60

Glu Asp Trp Gln Arg Val Val Ala Tyr Ala Arg Glu Glu Phe Gly Ser
65                   70                  75                  80

Val Asp Gly Leu Val Asn Asn Ala Gly Ile Ser Thr Gly Met Phe Leu
                 85                  90                  95

Glu Thr Glu Ser Val Glu Arg Phe Arg Lys Val Val Asp Ile Asn Leu
                100                 105                 110

Thr Gly Val Phe Ile Gly Met Lys Thr Val Ile Pro Ala Met Lys Asp
                115                 120                 125

Ala Gly Gly Gly Ser Ile Val Asn Ile Ser Ser Ala Ala Gly Leu Met
            130                 135                 140

Gly Leu Ala Leu Thr Ser Ser Tyr Gly Ala Ser Lys Trp Gly Val Arg
145                 150                 155                 160

Gly Leu Ser Lys Leu Ala Ala Val Glu Leu Gly Thr Asp Arg Ile Arg
                165                 170                 175

Val Asn Ser Val His Pro Gly Met Thr Tyr Thr Pro Met Thr Ala Glu
                180                 185                 190

Thr Gly Ile Arg Gln Gly Glu Gly Asn Tyr Pro Asn Thr Pro Met Gly
                195                 200                 205

Arg Val Gly Asn Glu Pro Gly Glu Ile Ala Gly Ala Val Val Lys Leu
                210                 215                 220

Leu Ser Asp Thr Ser Ser Tyr Val Thr Gly Ala Glu Leu Ala Val Asp
225                 230                 235                 240

Gly Gly Trp Thr Thr Gly Pro Thr Val Lys Tyr Val Met Gly Gln
                245                 250                 255
```

(2) INFORMATION FOR SEQ ID NO: 5:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 5:

```
Arg Gly Asp Ser
 1
```